(12) United States Patent
Darvesh et al.

(10) Patent No.: US 6,436,972 B1
(45) Date of Patent: Aug. 20, 2002

(54) PYRIDONES AND THEIR USE AS MODULATORS OF SERINE HYDROLASE ENZYMES

(75) Inventors: Sultan Darvesh, Halifax; David Magee; Zdenek Valenta, both of Fredericton; Earl Martin, Halifax, all of (CA)

(73) Assignee: Dalhousie University, Halifax (CA)

( * ) Notice: Subject to any disclaimer, the term of this patent is extended or adjusted under 35 U.S.C. 154(b) by 0 days.

(21) Appl. No.: 09/545,994

(22) Filed: Apr. 10, 2000

(51) Int. Cl.[7] ................. A61K 31/4406; C07D 213/00; C07D 213/44; C07D 213/82
(52) U.S. Cl. ....................... 514/355; 514/350; 514/374; 544/100; 546/300; 546/301
(58) Field of Search ................. 546/300, 301; 544/100; 514/350, 357, 355

(56) References Cited

U.S. PATENT DOCUMENTS

| | | | |
|---|---|---|---|
| 3,644,626 A | 2/1972 | Witzel | 424/263 |
| 3,655,897 A | 4/1972 | Witzel | 260/294.8 |
| 3,839,346 A | 10/1974 | Gadekar | 260/297 |
| 3,897,356 A | 7/1975 | Morisawa et al. | 424/263 |
| 4,092,410 A | 5/1978 | Ogata et al. | 424/78 |
| 4,465,686 A * | 8/1984 | Lesher et al. | 424/263 |
| 4,574,126 A | 3/1986 | Cooper et al. | 514/318 |
| 4,689,325 A | 8/1987 | Chu | 514/211 |
| 4,710,498 A | 12/1987 | Nohara et al. | 514/242 |
| 4,929,731 A | 5/1990 | Kozikowski et al. | 546/97 |
| 4,937,251 A | 6/1990 | Lunts | 514/351 |
| 5,104,880 A | 4/1992 | Kozikowski | 514/295 |
| 5,106,970 A | 4/1992 | Kozikowski et al. | 546/93 |
| 5,151,428 A | 9/1992 | Sakamoto et al. | 514/277 |
| 5,223,520 A | 6/1993 | Kristiansen et al. | 514/357 |
| 5,547,960 A | 8/1996 | Kozkowski et al. | 514/295 |
| 5,663,344 A | 9/1997 | Kozikowski et al. | 546/93 |
| 5,852,041 A | 12/1998 | Cosford et al. | 514/351 |
| 5,861,394 A * | 1/1999 | Urbahns et al. | 514/225.2 |
| 5,869,672 A | 2/1999 | Kozikowski et al. | 546/156 |
| 5,929,084 A | 7/1999 | Zhu et al. | 514/295 |

FOREIGN PATENT DOCUMENTS

| | | | | |
|---|---|---|---|---|
| EP | 05228369 | | 2/1993 | C07D/401/04 |
| EP | 462800 | * | 7/1996 | |
| WO | 9622021 | * | 7/1996 | |
| WO | 2000031021 | * | 7/1996 | |
| WO | 9955676 | * | 11/1999 | |
| WO | 0155132 | | 8/2000 | C07D/405/06 |

OTHER PUBLICATIONS

Kato et al.;"Antitumor activity—related compounds"; Yakugaku Zasshi 97/6,676–84 (1977).*
Chem.Abstracts: 120:134889; He et al (Chinese Chemical Letters, 4/7, 597–600(1993).*
Chem. Abstracts:96:210425; Maccari et al Lipids, 17/2, 78–83,(1982).*
Chem Abs: 125:142511 (Ishikawa, et al. *J. Mol. Catal. B: Enzym.* (1996) 1(3–6): 173–179).
Chem Abs: 120:134889 (He, et al. *Chinese Chemical Letters* (1993) 4(7):597–600).
Chem Abs: 96:210425 (Maccari, et al. *Lipids* (1982) 17(2):78–83).
Briaucourt, et al. *Chimica Therapeutica* (1973) 8(2):226–232.
Kozikowski, et al. *J. Med. Chem.* (1991) 34(12):3399–3402.
Hirota, et al. *Journal of Organic Chemistry* (1985) 50(9):1512–1516.
Anderson J.P. et al., "Exact cleavage site of Alzheimer amyloid precursor in neuronal PC–12 cells," *Neurosci. Lett.* 1991 Jul. 8;128(1):126–8.
Bartus, R.T. et al., "The cholinergic hypothesis of geriatric memory dysfunction," *Science*, 1982 Jul. 30;217(4558):408–14.
Boopathy, R. et al., "A peptidase activity exhibited by human serum pseudocholinesterase," *Eur. J. Biochem.* 1987 Jan. 2;162(1):191–7.
Coyle, J.T. et al., "Alzheimer's disease: a disorder of cortical cholinergic innervation," *Science*, 1983 Mar. 11;219(4589):1184–90.
Cummings, J.L. et al., "Alzheimer's disease: etiologies, pathophysiology, cognitive reserve, and treatment opportunities," *Neurology*, 1998; Jul.;51(1 Suppl 1):S2–17.

(List continued on next page.)

*Primary Examiner*—Mukund J. Shah
*Assistant Examiner*—Sudhaker B. Patel
(74) *Attorney, Agent, or Firm*—Lahive & Cockfield, LLP; Jane E. Remillard, Esq.; Richa Nand, Esq.

(57) ABSTRACT

This invention relates to a compound of formula I:

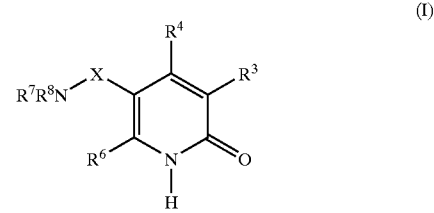

or a pharmaceutically acceptable salt thereof; in which preferably $R^3$, $R^4$ and $R^6$ are each hydrogen;

X is C=O or $CH_2$; and $R^7$ and $R^8$ are each independently selected from the group consisting of hydrogen, $(C_1-C_{12})$alkyl, $(C_3-C_8)$ cycloalkyl and $(C_1-C_{12})$alkyl$(C_6-C_{14})$aryl; or $R^7$ and $R^8$ when taken together form a $(C_2-C_7)$alkylene group; or —$NR^7R^8$ together forms a $(C_2-C_{14})$heterocyclic or substituted $(C_2-C_{14})$heterocyclic. Such compounds modulate the activity of serine hydrolases and can be used in pharmaceutical compositions for the treatment of Alzheimer's disease.

7 Claims, 6 Drawing Sheets

OTHER PUBLICATIONS

Darvesh, S. et al., "Enzyme kinetics of butyrylcholinesterase and trypsin: Implications in Alzheimer's disease," *Canadian Journal Neurological Sciences*, 1999; 26:S46–S47.

Ellman, G.L. et al., "A new and rapid colorimetric determination of acetylcholinesterase activity," *Biochemical Pharmacology*, 1961; 7:88–95.

Esch, F.S. et al., "Cleavage of amyloid beta peptide during constitutive processing of its precursor," *Science*, 1990 Jun. 1;248(4959):1122–4.

Geula, C. et al., "Special properties of cholinesterases in the cerebral cortex of Alzheimer's disease," *Brain Res.*, 1989 Sep. 25;498(1):185–9.

Geula, C. et al., "Cholinesterase and the pathology of Alzheimer disease," *Alzheimer Dis Assoc. Disord.* 1995;9 Suppl 2:23–8.

Greig, N.H., et al., "Novel, selective butyrylcholinesterase (BchE) inhibitors for the treatment of Alzheimer's disease(AD)," *Society for neuroscience abstracts*, 1998; 24:728.

Guillozet, A.L. et al., "Butyrylcholinesterase in the life cycle of amyloid plaques," *Ann. Neurol.* 1997 Dec.;42(6):909–18.

Haass, C. et al., "Cellular processing of beta–amyloid precursor protein and the genesis of amyloid beta–peptide," *Cell*, 1993 Dec. 17;75(6):1039–42.

Hardy, J., "Amyloid, the presenilins and Alzheimer's disease," *Trends Neurosci.*, 1997 Apr.;20(4):154–9.

Hooper, N.M. et al., "Membrane protein secretases," *Biochem. J.*, 1997 Jan. 15;321 (Pt 2):265–79.

Kitaguchi, N. et al., "Novel precursor of Alzheimer's disease amyloid protein shows protease inhibitory activty," *Nature*, 1988 Feb. 11;331(6156):530–2.

Layer, P.G., "Nonclassical roles of cholinesterases in the embryonic brain and possible links to Alzheimer disease," *Alzheimer Dis. Assoc. Disord.*, 1995;9 Suppl 2:29–36.

Lockridge, O., "Substance P hydrolysis by human serum cholinesterase," *J. Neurochem.*, 1982 Jul.;39(1):106–10.

Mayeux, R. et al., "Treatment of Alzheimer's disease," *N. Engl. J. Med.*, 1999 Nov. 25;341(22):1670–9.

Meckelein, B. et al., "Identification of a novel serine protease–like molecule in human brain," *Brain Res. Mol. Brain Res.*, 1998 Apr.;55(2):181–97.

Mesulam, M.–M. et al., "Butyrylcholinesterase reactivity differentiates the amyloid plaques of aging from those of dementia," *Ann. Neurol.*, 1994 Nov.;36(5):722–7.

Minn, A. et al., "Enhanced GFAP expression in astrocytes of transgenic mice expressing the human brain–specific trypsinogen IV," *Glia.*, 1998 Apr.;22(4):338–47.

Mirra, S.S. et al., "The Consortium to Establish a Registry for Alzheimer's Disease (CERAD). Part II. Standardization of the neuropathologic assessment of Alzheimer's disease," *Neurology*, 1991 Apr.;41(4):479–86.

Patterson, C.J.S. et al., "The recognition, assessment and management of dementing disorders: conclusions from the Canadian Consensus Conference on Dementia," *CMAJ*, 1999 Jun. 15;160(12 Suppl):S1–15.

Selkoe, D.J., "The molecular pathology of Alzheimer's disease," *Neuron.*, 1991 Apr.;6(4):487–98.

Serres, M. de et al., "Proteolysis as the secretase and amyloidogenic cleavage sites of the beta–amyloid precursor protein by acetylcholinesterase and butyrylcholinesterase using model peptide substrates," *Cell. Mol. Neurobiol.*, 1993 Jun.;13(3):279–87.

Seubert, P. et al., "Isolation and quantification of soluble Alzheimer's beta–peptide from biological fluids," *Nature*, 1992 Sep. 24;359(6393):325–7.

Small, D.H. et al., "Non–classical actions of cholinesterases: role in cellular differetiation, tumorigenesis and Alzheimer's disease," *Neurochem. Int.*, 1996 May–Jun.;28(5–6):453–83.

Tanzi, R.E. et al., "Protease inhibitor domain encode by an amyloid protein precursor mRNA associated with Alzheimer's disease," *Nature*, 1988 Feb. 11;331(6156):528–30.

Tomita, S. et al., "A basic amino acid in the cytoplasmic domain of Alzheimer's beta–amyloid precursor protein (APP) is essential for cleavage of APP at the alpha–site," *J. Biol. Chem.*, 1998 Jul. 24;273(30):19304–10.

Von Worthington, Enzymes and related biochemicals, *Worthington Enzyme Manual*, (1993) 374:377–381.

Wiegand, U. et al., "Cloning of the cDNA encoding human brain trypsinogen and characterization of its product," *Gene*, 1993 Dec. 22;136(1–2):167–75.

\* cited by examiner

PYRIDONES AND THEIR USE AS MODULATORS OF SERINE HYDROLASE ENZYMES

BACKGROUND OF THE INVENTION

Alzheimer's disease (AD) is a common neurodegenerative disorder causing dementia. The incidence of AD increases with age (1). The prevalence of dementia rises from 3% at age 65 years to 47% after age 85 years (1). The population of the elderly continues to rise and hence incidence of AD is also expected to rise. The frequency of dementia doubles every 5 years after the age of 60 years. In the United States, the annual cost for AD is estimated to be in excess of $60 billion annually (2, 3). With the rise in numbers of elderly individuals, the prevalence of AD is also expected to rise with concomitant rise in the cost for AD. Development of drugs to delay the progression of AD as well as provide symptomatic treatment of this disorder is thus of paramount importance (1, 2, 3).

In AD there are three major microscopic features that are recognized as the hallmarks of the disease, namely neuritic plaques (NP), neurofibrillary tangles (NFT) and amyloid angiopathy (AA) (4). In addition, there is widespread cell loss, particularly of cholinergic neurons in the brain (5). Loss of cholinergic cells leads to reduction in the levels of the neurotransmitter acetylcholine, its synthesizing enzyme choline acetyltransferase, as well as its deactivating enzyme acetylcholinesterase (AChE) (5, 6). Reduction of cholinergic neurotransmission leads to some of the symptoms of AD (6).

Although the level of AChE is reduced in AD, the level of the closely related enzyme butyrylcholinesterase (BuChE 3.1.1.8) is increased in AD brains (7). BuChE is found in all the neuropathological lesions associated with AD, namely, NP, NFT and AA (7). Importantly, BuChE is found in NP in brains of patients with AD. BuChE is found in a higher number of plaques in brains of elderly individuals with AD relative to those without AD (8). BuChE in Alzheimer brains requires 10–100 times the concentration of inhibitors to completely inhibit its esterase activity relative to BuChE in normal brains (9). It has been shown that some BuChE inhibitors not only improve cognition in an animal model but also reduce the production of β-amyloid which is one of the principal constituents of neuritic plaques (10).

From a neuropathology perspective, deposition of amyloid and formation of NP is one of the central mechanisms in the evolution of AD (11, 12). However, amyloid plaques are also found in brains of elderly individuals who do not have dementia (13). It has been suggested that the amyloid plaques in individuals without dementia are "benign" and they become "malignant", causing dementia, when they are transformed into plaques containing degenerated neurites (13). These plaques are called neuritic plaques (NP). The mechanism of transformation from "benign" to "malignant" plaques is as yet unknown. It has been suggested that BuChE may play a major role in this transformation based on the observation that BuChE is found predominately in plaques that contain dystrophic neurites and not in plaques without dystrophic neurites (13).

Taken together these observations suggest that in brains of patients with AD there is a significant alteration of the biochemical properties of BuChE that alters its normal regulatory role in the brain thus contributing to the pathology of AD.

Recently, a brain specific serine protease called trypsin IV has been isolated and it is presumed to be involved in APP processing (24). Amyloid precursor protein (APP) is a transmembrane glycoprotein, which possesses a Kunitz-type serine protease inhibitor domain. The APP may be involved in protease regulation in the brain (14, 15). Of particular importance is the fact that abnormally cleaved APP results in the formation of a 40–42 amino acid residue β-amyloid protein fragment. This fragment is the main constituent of NP (16).

The proteolytic sites in APP have been studied extensively (18). There are three known proteolytic sites. The first is the α-secretase site which when cleaved yields a 120 KDa fragment that does not accumulate in amyloid plaques (18). A basic amino acid residue such as arginine at this site is required for cleavage (19). Enzymes that require a basic amino acid residue at the cleavage site of their substrates are serine peptidases, such as trypsin. The second cleavage site, the γ-secretase site, cleaves at lys-28 (also a tryptic-site), which is the last amino acid of the extracellular APP domain (20). The third cleavage site, the β-secretase site, occurs at the N-terminus (21). The latter two sites lead to fragments that accumulate in amyloid plaques.

The enzymes that cleave amyloid precursor protein are called "secretases" but they have not been fully identified (22). It has been observed that a basic amino acid residue is required at some of the sites where APP undergoes proteolytic cleavage (19). Two well-known enzymes that cleave peptides at basic amino acid residue sites are trypsin and carboxypeptidase B (23). Both of these enzymes are mainly recognized as pancreatic enzymes involved in digestion, but trypsin-like serine proteases have been found in the brain and are thought to be involved in APP processing (24, 25, 26, 27). Interestingly, an enzyme with tryptic-like activity is closely associated with BuChE (28, 29). Recent observations that BuChE considerably enhances tryptic activity under normal circumstances (30, 31) and the observations that BuChE, which is found in high levels in NP, has altered biochemical properties, suggests that there may be a loss of regulation of tryptic activity, and other serine peptidase activity, associated with BuChE. This loss of regulation may play a role in abnormal proteolytic processing of APP. Recent evidence suggests that inhibition of BuChE enhances cognitive performance in rats, and that it promotes non-amyloidogenic processing of amyloid precursor protein (10).

Development of molecules that inhibit the activity of BuChE and/or AChE and simultaneously enhance the activity of serine proteases would not only provide symptomatic treatment of AD but would also lead to discovery of drugs that stop the progression of AD.

SUMMARY OF THE INVENTION

The present invention provides 2-pyridones that modulate serine hydrolase activity. They inhibit activity of BuChE and or AChE and stimulate activity of trypsin.

More specifically, the present invention provides a compound of formula I:

or a pharmaceutically acceptable salt thereof;

wherein X is C=O, C=S or CH$_2$;

$R^3$, $R^4$ and $R^6$ are each independently selected from the group consisting of hydrogen, (C$_1$–C$_{12}$)alkyl, substituted (C$_1$–C$_{12}$)alkyl, (C$_3$–C$_8$)cycloalkyl, substituted (C$_3$–C$_8$)cycloalkyl, (C$_2$–C$_{12}$)alkenyl, substituted (C$_2$–C$_{12}$)alkenyl, (C$_2$–C$_{12}$)alkynyl, substituted (C$_2$–C$_{12}$)alkynyl, (C$_6$–C$_{14}$)aryl, substituted (C$_6$–C$_{14}$)aryl, (C$_1$–C$_{12}$)alkyl (C$_6$–C$_{14}$)aryl, substituted (C$_1$–C$_{12}$)alkyl(C$_6$–C$_4$)aryl, (C$_6$–C$_{14}$)aryl(C$_1$–C$_{12}$)alkyl, substituted (C$_6$–C$_{14}$)aryl(C$_1$–C$_{12}$)alkyl, (C$_6$–C$_{14}$)aryl (C$_2$–C$_{12}$)alkenyl, substituted (C$_6$–C$_{14}$)aryl(C$_2$–C$_{12}$) alkenyl, (C$_6$–C$_{14}$)aryl(C$_2$–C$_{12}$)alkynyl, substituted (C$_6$–C$_{14}$)aryl(C$_2$–C$_{12}$)alkynyl, (C$_2$–C$_{14}$)heterocyclic, substituted (C$_2$–C$_{14}$)heterocyclic, trifluoromethyl, halogen, cyano and nitro;

—S(O)R', —S(O)$_2$R', —S(O)$_2$OR' and —S(O)$_2$NHR', wherein each R' is independently (C$_1$–C$_{12}$)alkyl, (C$_2$–C$_{12}$) alkenyl, (C$_2$–C$_{12}$)alkynyl or (C$_6$–C$_{14}$)aryl;

—C(O)R", wherein R" is selected from the group consisting of hydrogen, (C$_1$–C$_{12}$)alkyl, substituted (C$_1$–C$_{12}$) alkyl, (C$_3$–C$_8$)cycloalkyl, substituted (C$_3$–C$_8$)cycloalkyl, (C$_1$–C$_{12}$)alkoxy, (C$_1$–C$_{12}$)alkylamino, (C$_2$–C$_{12}$)alkenyl, substituted (C$_2$–C$_{12}$)alkenyl, (C$_2$–C$_{12}$)alkynyl, substituted (C$_2$–C$_{12}$)alkynyl, (C$_6$–C$_{14}$)aryl, substituted (C$_6$–C$_{14}$)aryl, (C$_6$–C$_{14}$)aryloxy, (C$_6$–C$_{14}$)arylamino, (C$_1$–C$_{12}$)alkyl (C$_6$–C$_{14}$)aryl, substituted (C$_1$–C$_{12}$)alkyl (C$_6$–C$_{14}$)aryl, (C$_6$–C$_{14}$)aryl (C$_1$–C$_{12}$)alkyl, substituted (C$_6$–C$_{14}$)aryl (C$_1$–C$_{12}$)alkyl, (C$_6$–C$_{14}$)aryl (C$_2$–C$_{12}$)alkenyl, substituted (C$_6$–C$_{14}$)aryl (C$_2$–C$_{12}$)alkenyl, (C$_6$–C$_{14}$)aryl (C$_2$–C$_{12}$) alkynyl, substituted (C$_6$–C$_{14}$)aryl (C$_2$–C$_{12}$)alkynyl, (C$_2$–C$_{14}$)heterocyclic, substituted (C$_2$–C$_{14}$)heterocyclic and trifluoromethyl;

—OR''' and —NR'''$_2$, wherein each R''' is independently selected from hydrogen, (C$_1$–C$_{12}$)alkyl, substituted (C$_1$–C$_{12}$)alkyl, (C$_3$–C$_8$)cycloalkyl, substituted (C$_3$–C$_8$) cycloalkyl, (C$_2$–C$_{12}$)alkenyl, substituted (C$_2$–C$_{12}$)alkenyl, (C$_2$–C$_{12}$)alkynyl, substituted (C$_2$–C$_{12}$)alkynyl, (C$_6$–C$_{14}$) aryl, substituted (C$_6$–C$_{14}$)aryl, (C$_1$–C$_{12}$)alkyl(C$_6$–C$_{14}$)aryl, substituted (C$_1$–C$_{12}$)alkyl(C$_6$–C$_{14}$)aryl, (C$_6$–C$_{14}$)aryl (C$_1$–C$_{12}$)alkyl, substituted (C$_6$–C$_{14}$)aryl(C$_1$–C$_{12}$)alkyl, (C$_6$–C$_{14}$)aryl (C$_2$–C$_{12}$)alkenyl, substituted (C$_6$–C$_{14}$)aryl (C$_2$–C$_{12}$)alkenyl, (C$_6$–C$_{14}$)aryl(C$_2$–C$_{12}$)alkynyl, substituted (C$_6$–C$_{14}$)aryl(C$_2$–C$_{12}$)alkynyl, (C$_6$–C$_{14}$)aroyl, substituted (C$_6$–C$_{14}$)aroyl, (C$_2$–C$_{14}$)heterocyclic, substituted (C$_2$–C$_{14}$) heterocyclic, (C$_1$–C$_{12}$)acyl and trifluoromethyl;

—SR"", wherein R"" is selected from the group consisting of hydrogen, (C$_1$–C$_{12}$)alkyl, substituted (C$_1$–C$_{12}$)alkyl, (C$_2$–C$_{12}$)alkenyl, substituted (C$_2$–C$_{12}$)alkenyl, (C$_2$–C$_{12}$) alkynyl, substituted (C$_2$–C$_{12}$)alkynyl, (C$_6$–C$_{14}$)aryl, substituted (C$_6$–C$_{14}$)aryl, (C$_1$–C$_{12}$)alkyl(C$_6$–C$_{14}$)aryl, substituted (C$_1$–C$_{12}$)alkyl(C$_6$–C$_{14}$)aryl, (C$_6$–C$_{14}$)aryl(C$_1$–C$_{12}$)alkyl, substituted (C$_6$–C$_{14}$)aryl(C$_1$–C$_{12}$)alkyl, (C$_6$–C$_{14}$)aryl (C$_2$–C$_{12}$)alkenyl, substituted (C$_6$–C$_{14}$)aryl(C$_2$–C$_{12}$)alkenyl, (C$_6$–C$_{14}$)aryl(C$_2$–C$_{12}$)alkynyl, substituted (C$_6$–C$_{14}$)aryl (C$_2$–C$_{12}$)alkynyl, (C$_2$–C$_{14}$)heterocyclic, substituted (C$_2$–C$_{14}$)heterocyclic and trifluoromethyl; and —SiR""'$_3$, wherein R""' is selected from (C$_1$–C$_{12}$)alkyl or (C$_6$–C$_{14}$)aryl; and $R^7$ and $R^8$ are each independently selected from the group consisting of hydrogen, (C$_1$–C$_{12}$)alkyl, substituted (C$_1$–C$_{12}$) alkyl, (C$_3$–C$_8$)cycloalkyl, substituted (C$_3$–C$_8$)cycloalkyl, (C$_2$–C$_{12}$)alkenyl, substituted (C$_2$–C$_{12}$)alkenyl, (C$_2$–C$_{12}$) alkynyl, substituted (C$_2$–C$_{12}$)alkynyl, (C$_6$–C$_{14}$)aryl, substituted (C$_6$–C$_{14}$)aryl, (C$_1$–C$_{12}$)alkyl(C$_6$–C$_{14}$)aryl, substituted (C$_1$–C$_{12}$)alkyl(C$_6$–C$_{14}$)aryl, (C$_6$–C$_{14}$)aryl(C$_1$–C$_{12}$)alkyl, substituted (C$_6$–C$_{14}$)aryl(C$_1$–C$_{12}$)alkyl, (C$_6$–C$_{14}$)aryl (C$_2$–C$_{12}$)alkenyl, substituted (C$_6$–C$_{14}$)aryl (C$_2$–C$_{12}$)alkenyl, (C$_6$–C$_{14}$)aryl (C$_2$–C$_{12}$)alkynyl, substituted (C$_6$–C$_{14}$)aryl (C$_2$–C$_{12}$)alkynyl, (C$_2$–C$_{14}$)heterocyclic, substituted (C$_2$–C$_{14}$)heterocyclic and trifluoromethyl; or

—NR$^7$R$^8$ forms a (C$_2$–C$_{14}$)heterocyclic or substituted (C$_2$–C$_{14}$)heterocyclic group;

wherein the substituted groups listed above are substituted with one or more substituents selected from the group consisting of hydroxy, (C$_1$–C$_4$)alkoxy, (C$_6$–C$_{14}$)aryl, (C$_2$–C$_{14}$)heterocyclic, halogen, trifluoromethyl, cyano, nitro, amino, carboxyl, carbamate, sulfonyl and sulfonamide,; and the heterocyclic group contains at least one atom, preferably two, selected from oxygen, nitrogen and sulfur.

The present invention also provides a pharmaceutical composition comprising a compound of formula I disclosed herein, or a pharmaceutically acceptable salt thereof, together with a pharmaceutically acceptable diluent or carrier. Preferably the pharmaceutical composition of the invention is for the modulation of an activity of a serine hydrolase.

Compounds of the formula I, while depicted herein in their "keto" tautomeric form, can also exist in their corresponding "enol" tautomeric form.

DETAILED DESCRIPTION OF THE INVENTION

As employed herein, "lower alkyl" refers to straight or branched chain alkyl groups having 1 to 4 carbon atoms; "alkyl" refers to straight or branched chain alkyl groups having 1 to 12 carbon atoms;

"substituted alkyl" refers to alkyl groups bearing one or more substituents such as hydroxy, ($C_1$–$C_4$)alkoxy, ($C_6$–$C_{14}$)aryl, ($C_2$–$C_{14}$)heterocyclic, halogen, trifluoromethyl, cyano, nitro, amino, carboxyl, carbamate, sulfonyl, sulfonamide, and the like;

"cycloalkyl" refers to cyclic ring-containing groups containing 3 to 8 carbon atoms, and "substituted cycloalkyl" refers to cycloalkyl groups bearing one or more substituents as set forth above;

"alkenyl" refers to straight or branched chain hydrocarbyl groups having at least one carbon-carbon double bond, and having 2 to 12 carbon atoms (with groups having 2 to 6 carbon atoms presently being preferred), and "substituted alkenyl" refers to alkenyl groups bearing one or more substituents as set forth above;

"alkynyl" refers to straight or branched chain hydrocarbyl groups having at least one carbon-carbon triple bond, and having 2 to 12 carbon atoms (with groups having 2 to 6 carbon atoms presently being preferred), and "substituted alkynyl" refers to alkynyl groups bearing one or more substituents as set forth above;

"aryl" refers to aromatic groups having 6 to 14 carbon atoms and "substituted aryl" refers to aryl groups bearing one or more substituents as set forth above;

"alkylaryl" refers to alkyl-substituted aryl groups and "substituted alkylaryl" refers to alkylaryl groups bearing one or more substituents as set forth above;

"arylalkyl" refers to aryl-substituted alkyl groups and "substituted arylalkyl" refers to arylalkyl groups bearing one or more substituents as set forth above;

"arylalkenyl" refers to aryl-substituted alkenyl groups and "substituted arylalkenyl" refers to arylalkenyl groups bearing one or more substituents as set forth above;

"arylalkynyl" refers to aryl-substituted alkynyl groups and "substituted arylalkynyl" refers to arylalkynyl groups bearing one or more substituents as set forth above;

"aroyl" refers to aryl-carbonyl species such as benzoyl and "substituted aroyl" refers to aroyl groups bearing one or more substituents as set forth above;

"heterocyclic" refers to cyclic (i.e., ring containing) groups containing one or more heteroatoms (e.g., N, O, S, or the like) as part of the ring structure, and having 2 to 14 carbon atoms and "substituted heterocyclic" refers to heterocyclic groups bearing one or more substituents as set forth above;

"acyl" refers to alkyl-carbonyl species; and

"halogen" refers to fluoride, chloride, bromide or iodide groups.

In preferred embodiments of the invention, $R^3$, $R^4$ and $R^6$ are each hydrogen.

In further preferred embodiments of the invention, X is C=O or $CH_2$.

In further preferred embodiments of the invention $R^7$ and $R^8$ are each independently selected from the group consisting of hydrogen, ($C_1$–$C_{12}$)alkyl, ($C_3$–$C_8$)cycloalkyl and ($C_1$–$C_{12}$)alkyl ($C_6$–$C_{14}$)aryl; or —$NR^7R^8$ together forms a ($C_2$–$C_{14}$)heterocyclic or substituted ($C_2$–$C_{14}$)heterocyclic group. Preferably the heterocyclic or substituted heterocyclic group includes a further heteroatom selected from nitrogen, sulfur and oxygen, and more preferably includes one or more fused benzo groups.

Also preferred are compounds in which, in —$NR^7R^8$, $R^7$ and $R^8$ together form a ($C_2$–$C_7$)alkylene group.

More preferred is a compound selected from the group consisting of:

5-(N,N-dibenzyl)aminocarbonyl-2-pyridone;
5-(N,N-diisopropyl)aminocarbonyl-2-pyridone;
5-(N,N-diethyl)aminocarbonyl-2-pyridone;
5-(N,N-diethyl)aminomethyl-2-pyridone;
5-(1-pyrrolidinyl)aminocarbonyl-2-pyridone;
5-(1-piperidinyl)aminocarbonyl-2-pyridone;
5-(N-cyclohexyl)aminocarbonyl-2-pyridone;
5-(N-phenothiazinyl)aminocarbonyl-2-pyridone;
5-(N-phenoxazinyl)aminocarbonyl-2-pyridone; and
5-(N-(N-methyl)piperazinyl)aminocarbonyl-2-pyridone.

The compounds of the invention modulate serine hydrolase activity.

Certain compounds of the invention are effective as inhibitors of cholinesterases, for example butyrylcholinesterase (BuChE) and acetylcholinesterase (AChE).

Certain compounds of the invention are effective in enhancing the activity of serine proteases, for example trypsin and a trypsin-like protein associated with BuChE in a brain of a mammal, such as a human.

The compounds of the invention can be used to treat, inhibit or prevent a pathological condition that is manifested in an abnormal concentration of, and/or activity of, a serine hydrolase enzyme. Among those pathological conditions are Alzheimer's disease, tumours such as brain tumours, for example gliomas, and glaucoma.

Materials and Methods
Synthesis of 2-Pyridone Compounds

The synthesis of exemplified 2-pyridone compounds was achieved in significant yield in a two-step, one pot procedure.

Amides

Scheme I shows a method of preparing amide compounds of the invention in which $R^3$, $R^4$ and R6 are hydrogen. 6-hydroxy nicotinic acid is a readily available starting material. It can be converted to the corresponding acid chloride with thionyl chloride which in turn can be used to synthesize a variety of substituted amides of the general formula I in significant yield.

Amines

Scheme II shows a method of preparing preferred amine compounds of the invention in which $R^3$, $R^4$ and $R^6$ are hydrogen. The acid chloride of 6-hydroxy-nicotinic acid can be treated with methanol to give the corresponding methyl ester, which can be reduced with lithium aluminum hydride to the corresponding 5-hydroxy methyl 2-pyridone. This can be converted to the corresponding bromide with hydrobromic acid. The 5-bromo methyl-2-pyridone can then be used to synthesize a variety of substituted amines of the general formula I in significant yield.

Example 1

5-(N,N-dibenzyl)aminocarbonyl-2-pyridone (tautomer form N,N-Dibenzyl 6-hydroxynicotinamide).

N,N-Dibenzyl 6-hydroxynicotinamide was made according to the above procedure using 1.58 g (10.0 mmol) of 6-hydroxynicotinyl chloride and 2.3 ml (12.0 mmol) of dibenzylamine to furnish 1.84 g (58%) of product. $^1$H NMR (CDCl$_3$, 200 MHz) δ:7.73 (d, J=3.0 Hz, 1H), 7.65 (dd, J=9.0, 4.5 Hz, 1H), 7.45–7.13 (m, 11H), 6.51 (d, J=9.0 Hz, 1H), 4.57 (bs, 4H). IR (CHCl$_3$) cm$^{-1}$: 3387, 3011, 1681, 1660, 1633, 1223. HREIMS m+/z (%): C$_{20}$H$_{18}$N$_2$O$_2$ (calc)= 318.1369; C$_{20}$H$_{18}$N$_2$O$_2$ (obs)=318.1359 (90).

Example 2

5-(N,N-diisopropyl)aminocarbonyl-2-pyridone.

A 200 ml round bottomed flask (RBF) was charged with 1.13 g (7.18 mmol) of 6-hydroxynicotinyl chloride in 100 ml of methylene chloride, cooled and stirred at 0° C. N,N-diisopropylamine (8.6 mM=0.85 ml) in 10 ml methylene chloride was added drop wise and the resulting mixture was stirred at room temperature for 15 hours. The mixture was then concentrated under vacuum. To the residue was added 25 ml of methylene chloride and stirred at 30° C. for 5 minutes. Solid was filtered and residue was chromatographed using CH$_2$Cl$_2$:MeOH:NH$_3$=200:10:1. The product was recrystallized from CH$_2$C$_{12}$ and petroleum ether (yield 29%). $^1$H NMR (CD$_3$OD, 400 MHz, ppm) 7.58 (s, 1H), 7.56 (dd, J=2.6 , 9 Hz, 1H), 6.57 (dd, J=1.0, 9.06 Hz, 1H), 5.21 (bs, 1H), 3.80 (bs, 2H), 1.34 (m, 12H). $^{13}$C NMR (CD$_3$OD, 400 MHz, ppm): 167.8, 163.6, 140.0, 134.2, 119.4, 117.8, 49.0, 19.7. IR (CHCl$_3$) cm$^{-1}$: 3371, 3118, 2918, 2852, 1600, 1433, 1366, 1335, 1128, 1090, 882, 597. HREIMS m+/z (%) C$_{12}$H$_{18}$N$_2$O$_2$ (calc)=222.1368, C$_{12}$H$_{18}$N$_2$O$_2$ (obs)= 222.1362 (100).

Example 3

5-(N,N-diethyl)aminocarbonyl-2-pyridone.

5-(N,N-diethyl)aminocarbonyl-2-pyridone was synthesized according to the general procedure outlined above. Briefly, 1.58 g (10.0 mmol) of 6-hydroxynicotinyl chloride was reacted with 2.07 ml (20.0mmol) of diethylamine to furnish 0.87 g of the product. $^1$H NMR (DMSO-d$_6$, 400 MHz) δ:11.60 (bs, 1H), 7.47 (s, 1H), 7.43 (d, J=9.4 Hz, 1H), 6.32 (d, J=9.4 Hz, 1H), 3.40–3.31 (bq, 6.7 Hz, 4H), 1.09 (t, J=6.7 Hz, 6H). $^{13}$C NMR(DMSO-d$_6$, 400 MHz) δ:166.7, 161.6, 139.4, 135.3, 119.1, 114.3, 40.9, 40.1, 13.2. IR (CHCl$_3$) cm$^{-1}$: 3370, 3120, 2915, 2860, 1605, 1430, 1366, 1335, 1135, 1080, 882, 605. HREIMS m+/z (%): C$_{10}$H$_{14}$N$_2$O$_2$ (calc)=194.1056; C$_{10}$H$_{14}$N$_2$O$_2$ (obs)= 194.1055 (100).

Example 4

5-(N,N-diethyl)aminomethyl-2-pyridone.

6-hydroxy nicotinic acid (2 gm, 14.4 mmol) was mixed with 4.6 ml of thionyl chloride and refluxed until clear and the mixture was maintained at 80° C. for 20 min. The excess thionyl chloride was evaporated in vacuo. The cooled 6-hydroxynicotinyl chloride was treated with 10 ml of methanol and the solution was refluxed for 1 hour. The excess methanol was evaporated and the methyl 6-hydroxy nicotinate was crystallized from acetone. The yield of the product was 1.88 gm (85%). $^1$H NMR (d$_6$-DMSO, ppm); 11.8 (broad, H, NH), 8.03 (d, J=2.7 Hz, 1H, C(6)H), 7.78 (dd, J$_{3-4}$=9.6, J$_{4-6}$=2.7 Hz, 1H C(4)H), 6.35(d, J=9.6 Hz, 1H, C(3)H), 3.75 (s, 3H, CH$_3$O).

To a suspension of LiAlH$_4$ (0.32 gm, 8.4 mmol) in 80 ml THF was added, slowly and dropwise, a solution of methyl 6-hydroxynicotinate (1.15 gm, 7.5 mmol) in 400 ml THF. The mixture was stirred at room temperature for 1.5 hours and then refluxed for 10 minutes. The mixture was then cooled and the reaction quenched with 3.0 ml of ethyl acetate and 1.5 ml of water. The solvents were removed and the residue was taken up in 40 ml of refluxing ethanol. The solution was filtered through celite and ethanol was evaporated in vacuo. The product was purified by silica gel chromatography using ethyl acetate/methanol (2:1) as the eluent. The product 5-hydroxymethyl-2-pyridone was crystallized from ethanol/ethyl acetate and the yield of the reaction was 0.65 gm (80%). HRMS: m/e, M$^+$ found 125.0468, 100%. Calc. for C$_6$H$_7$NO$_2$: 125.0477, –6 ppm. $^1$H NMR (d$_6$-DMSO): 11.47 (broad, 1H, NH), 7.39 (dd, J$_{3-4}$= 9.5 Hz, J$_{4-6}$=2.5 Hz, 1H, C(4)H), 7.23 (d, J$_{4-6}$=2.5 Hz, 1H, C(6)H), 6.27 (d, J$_{3-4}$=9.5 Hz, 1H, C(3)H), 5.10 (t, J=5.5 Hz, 1H, CH$_2$OH), 4.17 (d, J=5.5 Hz, 2H, CH$_2$OH). IR (cm$^{-1}$): 3271 (m, broad), ν(O—H); 3124 (m, broad), ν(N—H); 3011(m), ν(C—H); 1661(vs), ν (C=O).

To 5-hydroxymethyl-2-pyridone (114.9 mg, 0.9 mmol) was added 3.0 ml of 48% hydrobromic acid. The mixture was heated at 100° C. for 20 minutes. The excess hydrobromic acid was then evaporated in vacuo to give the corresponding 5-bromomethyl-2-pyridone. This compound was used without purification. HRMS: m/e, M+found; 186.9626, 7.4% Calc. for $C_6H_6BrNO$: 186.9633, −3.9 ppm.

The 5-bromomethyl-2-pyridone was taken up in diethyl amine and the solution refluxed for 1 hour. The solution was then treated with 10% sodium hydroxide at 0° C. and washed with chloroform. The aqueous phase was treated with hydrochloric acid to a pH of 6.0 and extracted with chloroform/methanol (5:1). The solution was dried over $Na_2SO_4$ and the solvent was then evaporated. The product, (N,N-diethylaminomethyl)-2-pyridone, was obtained in 34% yield. HRMS: m/e, M+ found; 180.1251, 20.8%. Calc. for $C_{10}H_{16}N_2O$; 180.1263, −6.3 ppm. $^1H$ NMR (ppm): 13.1 (broad, 1H, NH), 7.49 (dd, $J_{3-4}$=9.2 Hz, $J_{4-6}$=2.4 Hz, 1H, C(4)H), 7.25 (d, $J_{4-6}$=2.4 Hz, 1H, C(6)H), 6.55 (d, $J_{3-4}$=9.2 Hz, 1H, C(3)H), 3.30 (s, 2H, $CH_2O$), 2.45 (q, J=7.1 Hz, 4H, $N(CH_2CH_3)_2$), 1.00 (t, J=7.1 Hz, 6H, $N(CH_2CH_3)_2$). IR ($cm^{-1}$) : 1660(vs), ν(C=O).

Example 5

5-(1-pyrrolidinyl)aminocarbonyl-2-pyridone.

In a 250 ml RBF was put 2.6 g of 6-hydroxynicotinic acid and to this was added 25 ml of $SOCl_2$. The flask was then equipped with a reflux condenser and a $CaCl_2$ drying tube. The slurry was brought to reflux and after 30–45 minutes the solution became homogenous. The solution was then refluxed for an additional 15 minutes and then the $SOCl_2$ was immediately evaporated in vacuo and then put on a vacuum pump for half an hour. The solid was then taken up in $CH_2Cl_2$ (225 mls) and 1.9 mls of freshly distilled pyrrolidine was added dropwise over 2 minutes. The solution was then stirred at room temperature for 16 hours under an inert atmosphere. The reaction mixture was concentrated to approximately 75 mls and then was filtered through a pad of celite. The filtrate was evaporated to dryness to give a tan colored glass. The solid was taken up in $CH_2Cl_2$ ((50 mls) and washed with 1 M NaOH (4×25 mls). Combined aqueous phase was acidified by addition of 10 mls of conc. HCl and then extracted with n-BuOH (4×25 mls). The combined organic phase was washed with saline (1×) and then dried (MgSO4), filtered and solvent evaporated to give a tan colored solid. Purified on SiO2 (10:1 $CH_2Cl_2$/MeOH as eluent) and crystallized from $CH_2Cl_2$/petroleum ether to furnish 1.08 g (56%) of product. $^1H$ NMR ($CDCl_3$, 400 MHz) δ:7.71 (s, 1H), 7.63 (d, J=8.5 Hz, 1H), 6.44 (d, J=8.6 Hz, 1H), 3.45 (m, 4H), 1.82 (m, 4H). $^{13}C$ NMR ($CDCl_3$, 400 MHz) d: 165.4, 164.5, 140.8, 136.4, 119.4, 116.3, 49.5, 46.7, 26.5, 24.1. IR ($CHCl_3$) $cm^{-1}$: 3365, 3113, 2905, 2823, 1650, 1570, 1483, 1335, 1120, 827, 608. HREIMS m+/z (%): $C_{10}H_{12}N_2O_2$ (calc)=192.0900; $C_{10}H_{12}N_2O_2$ (obs)= 192.0892 (85).

Example 6

5-(1-piperidinyl)aminocarbonyl-2-pyridone
(tautomer form Piperidinyl-6-hydroxynicotinamide).

A 100 ml RBF was charged with 6-hydroxynicotinic acid (4 g) and 20 ml of thionyl chloride. The mixture was refluxed for 1 hr. Excess thionyl chloride was then evaporated in vacuo to obtain the 6-hydroxynicotinyl chloride. A 200 ml RBF was charged with 1.13 g of 6-hydroxynicotinyl chloride in 100 ml of methylene chloride, cooled and stirred at 0° C. Piperidine (8.6 mM=0.85 ml) in 10 ml methylene chloride was added dropwise and the resulting mixture was stirred at room temperature for 15 hours. The mixture was then concentrated under vacuum. To the residue was added 25 ml of methylene chloride and stirred at 30° C. for 5 minutes. Solid was filtered and residue was chromatographed using $CH_2C_{12}$:MeOH:$NH_3$=200:10:1. The product was recrystallized from $CH_2Cl_2$ and petroleum ether to furnish 0.92 g (62%) of product. $^1H$ NMR ($CDCl_3$, 400 MHz) δ: 7.61 (s, 1H), 7.55 (d, J=8.4 Hz, 1H), 6.55 (d, J=8.6 Hz, 1H), 3.50 (bs, 4H), 1.65 (m, 2H), 1.57 (m, 4H). $^{13}C$ NMR ($CDCl_3$, 400 MHz) δ:166.5, 164.8, 141.3, 135.7, 119.7, 116.1, 26.0, 24.4. IR ($CHCl_3$) $cm^{-1}$: 3346, 3050, 3004, 1655, 1615, 1473, 1115, 841, 780, 627. HREIMS m+/z (%) : $C_{11}H_{14}N_2O_2$ (calc)=206.1055; $C_{11}Hl_{14}N_2O_2$ (obs)=206.1061 (70).

Example 7

5-(N-cyclohexyl)aminocarbonyl-2-pyridone
(tautomer form N-Cyclohexyl 6-hydroxynicotinamide).

N-Cyclohexyl 6-hydroxynicotinamide was synthesized according to the general procedure using 1.58 g (10.0 mmol) of 6-hydroxynicotinyl chloride and 1.37 ml (12.0 mmol) of cyclohexylamine to furnish 1.54 g (70%) of the product. $^1H$ NMR ($CD_3OD$, 400 MHz) δ:8.03 (s, 1H), 7.97 (d, J=8.4 Hz, 1H), 6.52 (d, J=8.6 Hz, 1H), 3.98 (m, 4H), 1.92 (m, 2H), 1.78 (m, 2H), 1.68 (m, 1H), 1.32 (m, 5 H). $^{13}C$ NMR ($CD_3OD$, 400 MHz) δ:164.2, 164.1, 139.7, 136.8, 118.6, 114.6, 49.1, 48.2, 46.9, 32.3, 25.2, 25.0. IR (Nujol) $cm^{-1}$: 3294, 3062, 1637, 1545. HREIMS m+/z (%): $C_{12}H_{16}N_2O_2$ (calc)=220.1212; $C_{12}H_{16}N_2O_2$ (obs)=220.1205 (100).

Example 8

5-(N-phenothiazinyl)aminocarbonyl-2-pyridone
(tautomer form Phenothiazinyl 6-hydroxynicotinamide).

Phenothiazinyl 6-hydroxynicotinamide was synthesized according to the general procedure using 1.2 g (7.6 mmol) of 6-hydroxynicotinyl chloride and 2.93 g (14.7 mmol) of phenothiazine to furnish 0.71 g (31%) of product. $^1H$ NMR (DMSO-$d_6$, 400 MHz) δ:11.85 (bs, 1H), 7.62–7.57 (m, 4H), 7.44 (d, J=2.6 Hz, 1H), 7.35–7.25 (m, 4H), 7.05 (dd, J=9.8, 2.7 Hz, 1H), 6.12 (d, J=9.6 Hz, 1H). $^{13}C$ NMR (DMSO-$d_6$, 400 MHz) δ:164.9, 161.9, 140.2, 139.4, 131.7, 128.3, 127.8, 127.3, 127.3, 119.0, 112.9. IR (KBr) $cm^{-1}$: 3446, 3070, 3054, 1645, 1615, 1460, 1351, 1266, 1114, 841, 780, 627. HREIMS m+/z (%) $C_{18}H_{12}N_2O_2S$ (calc)=320.0621; $C_{18}H_{12}N_2O_2S$ (obs)=320.0622 (100).

Example 9

5-(N-phenoxazinyl)aminocarbonyl-2-pyridone
(tautomer form Phenoxazinyl 6-hydroxynicotinamide).

Phenoxazinyl 6-hydroxynicotinamide was prepared according to the general procedure using 0.387 g (2.8 mmol) of 6-hydroxynicotinyl chloride and 0.503 g (2.7 mmol) of phenoxazine to furnish 0.136 g (16%) of product. $^1H$ NMR (DMSO-$d_6$, 400 MHz) d: 11.81 (bs, 1H), 7.62 (bs, 1H), 7.52 (bs, 1H), 7.25 (m, 6H), 7.11 (m, 2H), 6.17 (d, J=10.4 Hz, 1H). IR (KBr) $cm^{-1}$: 3445, 3070, 3050, 1645, 1615, 1480, 1345, 1265, 1115, 620. HREIMS m+/z (%): $C_{18}H_{12}N_2O_3$ (calc)=304.0849; $C_{18}H_{12}N_2O_3$ (obs)=304.0854 (100).

Example 10

5-(N-(N-methyl)piperazinyl)aminocarbonyl-2-pyridone (tautomer form 1-Methylpiperazinyl 6-hydroxynicotinamide).

1-Methylpiperazinyl 6-hydroxynicotinamide was prepared according to the general procedure using 1.58 g (10.0 mmol) of 6-hydroxynicotinyl chloride and 1.00 g (10.0 mmol) of 1-methylpiperazine to furnish 0.85 g (38%) of product. $^1$H NMR (CDCl$_3$, 400 MHz) δ:7.72 (d, J=3.1 Hz, 1H), 7.60 (dd, J=3.1, 8.8 Hz, 1H), 6.59 (d, J=8.6 Hz, 1H), 3.67 (bt, J=4.5 Hz, 4H), 2.47 (t, J=4.6 Hz, 4H), 2.35 (s, 3H). IR (CHCl$_3$) cm$^{-1}$: 3007, 2946, 2803, 1681, 1660, 1632, 1614, 1459, 1435, 1297, 1275, 1137, 1000, 731, 664. HREIMS m+/z (%): C$_{11}$H$_{15}$N$_3$O$_2$ (calc)=221.1161; C$_{11}$H$_{15}$N$_3$O$_2$ (obs)=221.1163 (100).

Esterase Activity Assay

The esterase activity of BuChE or AChE was determined by a modification of the method described by Ellman et al. (32), using a buffered 5,5'-dithiobis(2-nitrobenzoic acid) (DTNB) solution. Stock DTNB solution consisted of 10 mM DTNB with 18 mM sodium bicarbonate in 0.1 M phosphate buffer, pH 7.0. Working DTNB solution was prepared by mixing 3.6 mL of 10 mM stock DTNB solution with 96.4 mL of 0.1 M phosphate buffer at pH 8.0. The assay was carried out by mixing 2.7 mL of buffered DTNB working solution (pH 8.0), 0.1 mL of BuChE or AChE in 0.005% aqueous gelatin (1 U/mL), and 0.1 mL of 50% aqueous acetonitrile, or a solution of a 2-pyridone compound of the invention in the same solvent, in a quartz cuvette of 1 cm path-length. Absorbance of this solution was calibrated to zero and the reaction was commenced by adding 0.1 mL of aqueous acetylthiocholine (AcSCh) or butyrylthiocholine (BuSCh) solutions of varying concentration (between 1.9 mM and 15 mM). The final volume was always 3.0 mL. The reactions were carried out at room temperature. The rate of change of absorbance (ΔA/min), reflecting the rate of hydrolysis of BuSCh or AcSCh, was recorded every 5 seconds for a total of 1 minute using a Milton-Roy uv-visible spectrophotometer set at λ=412 nm.

The slopes of Lineweaver-Burk plots versus Log of inhibitor concentration were used to determine the inhibitor constant K$_i$.

Trypsin Activity Assay

The effect of 2-pyridone compounds on trypsin-like enzymatic activity associated with BuChE and that of human trypsin was determined using Nα-benzoyl-DL-arginine-p-nitroanilide (BAPNA) as the substrate. The same procedure was used to study the effect of the compounds on BuChE-trypsin mixture. Reactions were performed in 0.06 M Tris buffer at pH 8.0. Phosphate buffer was not used because BAPNA was found to undergo buffer-catalyzed hydrolysis in this medium at pH 8.0 over prolonged periods. The incubations were carried out in 1.5 mL Eppendorf tubes by mixing 0.85 mL of 0.06 M Tris buffer (pH 8.0), 0.07 mL of up to 10 mM BAPNA, 0.03 mL of 50% aqueous acetonitrile, or a solution of 2-pyridone compound (typically, a 5 mM working solution) in the same solvent, and 0.05 mL of the enzyme solution (0.5–1.5 U of trypsin in 1 mM hydrochloric acid, or up to 5.0 U of BuChE in 0.005% aqueous gelatin). The final volume of the assay mixture was always 1.0 mL. The enzyme reaction mixture was incubated at 40° C. for 15–45 hours. The use of 1.5 U of trypsin gave an amount of p-nitroaniline (PNA) produced upon cleavage of BAFNA by trypsin after 22 hours of incubation that was similar to the amount of product formed by trypsin-like activity associated with 5 U of BuChE under the same conditions.

The concentration of the PNA was determined by means of high performance liquid chromatography (HPLC). This was carried out by injecting 20 μL samples of the reaction mixture into a Waters system consisting of a 501 pump, a 484 tunable uv-visible detector set at λ=380 nm to detect PNA, and a 745 data module. The column was a Nova-Pak C-18, 4μ cartridge (5 mm×10 cm) in a RCM 8×10 Radial Pak cartridge holder. The solvent was 50% aqueous methanol at a flow rate of 1.5 mL/min. PNA is detected at 380 nm where BAPNA does not absorb. A standard curve was generated by injecting known amounts of PNA into the HPLC system. At concentrations between 0.03–1.0 nmol of PNA a linear relationship between the concentration of the product and the integrated area under the curve was observed. The rate of formation of PNA was calculated by using the following formula: nmol of PNA /L/h=[integrated area under the curve×10$^5$]÷[integrated area for 1 nmol of PNA ×time of incubation (h)].

Scheme I

Scheme II

-continued

TABLE 1

Pyridone compounds

| Example | R⁷R⁸N = | X = |
|---|---|---|
| 1 | N-methyl-N,N-dibenzylamine | C=O |
| 2 | N-methyl-N,N-diisopropylamine | C=O |
| 3 | N-methyl-N,N-diethylamine | C=O |

TABLE 1-continued

Pyridone compounds

| Example | R⁷R⁸N = | X = |
|---|---|---|
| 4 | N-methyl-N,N-diethylamine | $CH_2$ |
| 5 | pyrrolidinyl | C=O |
| 6 | piperidinyl | C=O |
| 7 | N-cyclohexylamino | C=O |
| 8 | phenothiazinyl | C=O |
| 9 | phenoxazinyl | C=O |
| 10 | 4-methylpiperazinyl | C=O |

Esterase in Vitro Assay

The effect of increasing amount of exemplified 2-pyridone compounds (Examples 1 to 10) on the activity of human BuChE and AChE is shown in FIGS. 1 to 10.

The compounds of Examples 1 to 9 inhibited BuChE and AChE to varying degrees. Graphs of the slopes obtained from Lineweaver-Burk double reciprocal graphs versus log of the concentration of each compound gave the inhibition constant $K_i$ for each compound. These values are shown in Table 2.

TABLE 2

Inhibition constants for 2-pyridone compounds of the invention.

| | Esterase $K_i$ (M) | |
|---|---|---|
| Pyridone compound | BuChE (h) | AChE (h) |
| Example 1 | $3.75 \times 10^{-5}$ | $2.6 \times 10^{-4}$ |
| Example 2 | $1.43 \times 10^{-3}$ | $1.31 \times 10^{-4}$ |
| Example 3 | $1.3 \times 10^{-3}$ | $7.6 \times 10^{-3}$ |
| Example 4 | $3.89 \times 10^{-3}$ | $4.77 \times 10^{-3}$ |
| Example 5 | $5.18 \times 10^{-4}$ | Insignificant inhibition |
| Example 6 | $4.51 \times 10^{-3}$ | $1.3 \times 10^{-2}$ |
| Example 7 | $1.37 \times 10^{-4}$ | Insignificant inhibition |
| Example 8 | $4.29 \times 10^{-5}$ | Insignificant inhibition |
| Example 9 | $4.29 \times 10^{-5}$ | Insignificant inhibition |

Trypsin in Vitro Assay

Figure 1:
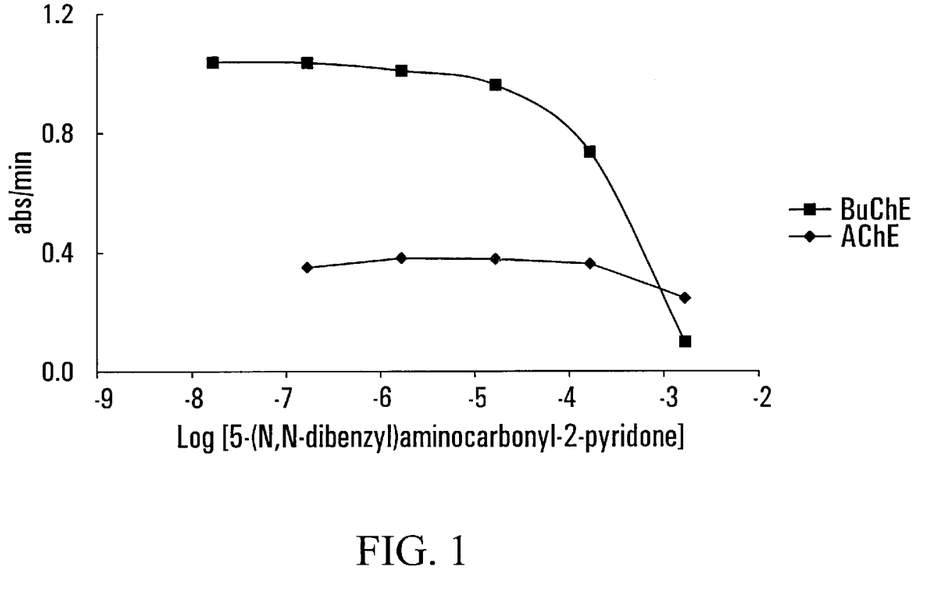
FIG. 1 is a plot of absorbance per minute against the log of concentration of 5-(N,N-dibenzyl)aminocarbonyl-2-pyridone. The graph reflects the rate of hydrolysis of the substrate (acetylthiocholine (AcSCh) for AChE and butyrylthiocholine (BuSCh) for BuChE).
Figure 2:
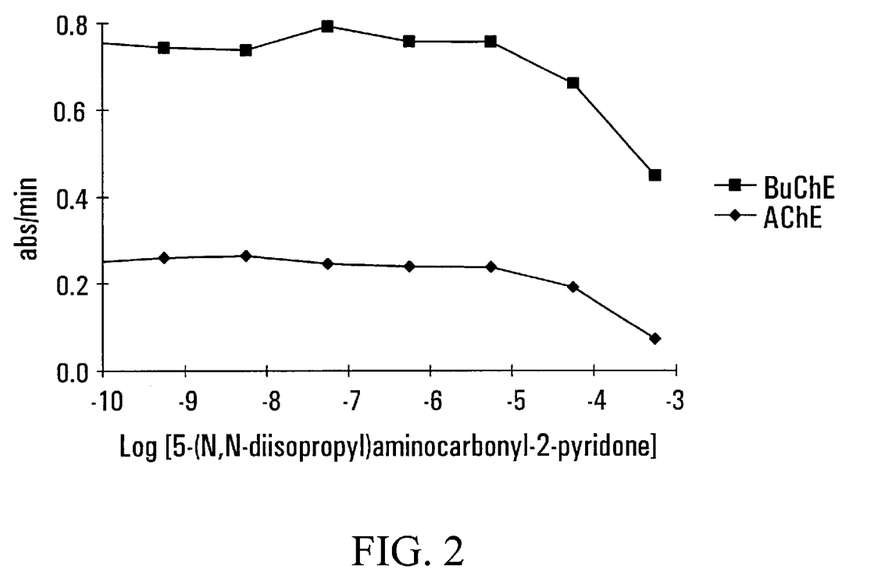
FIG. 2 is a plot of absorbance per minute against the log of concentration of 5-(N,N-diisopropyl)aminocarbonyl-2-pyridone. The graph reflects the rate of hydrolysis of the substrate (acetylthiocholine for AChE and butyrylthiocholine for BuChE).
Figure 3:
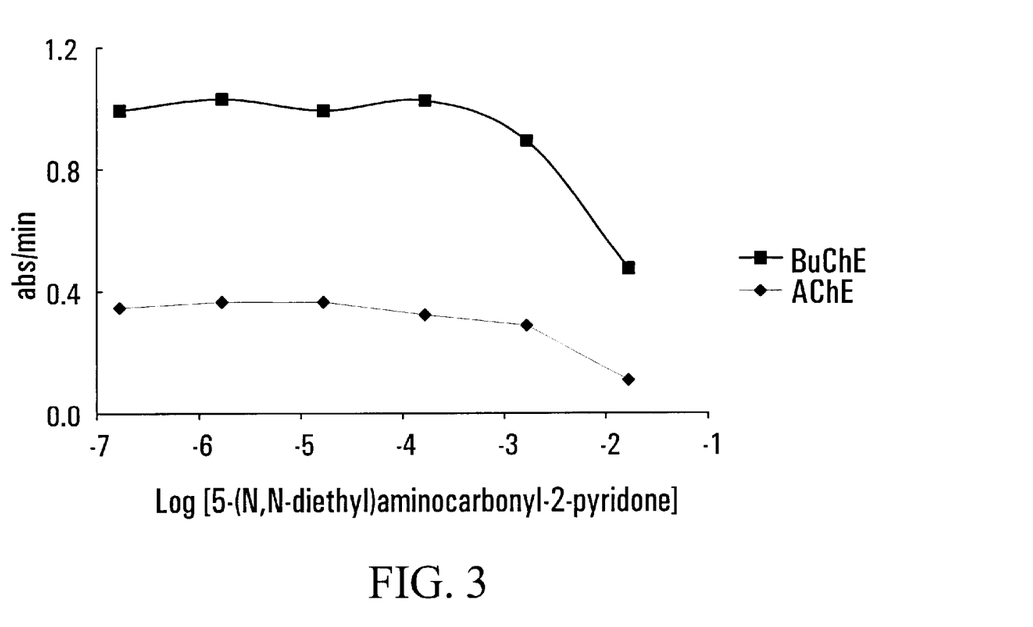
FIG. 3 is a plot of absorbance per minute against the log of concentration of 5-(N,N-diethyl)aminocarbonyl-2-pyridone. The graph reflects the rate of hydrolysis of the substrate (acetylthiocholine for AChE and butyrylthiocholine for BuChE).
Figure 4:
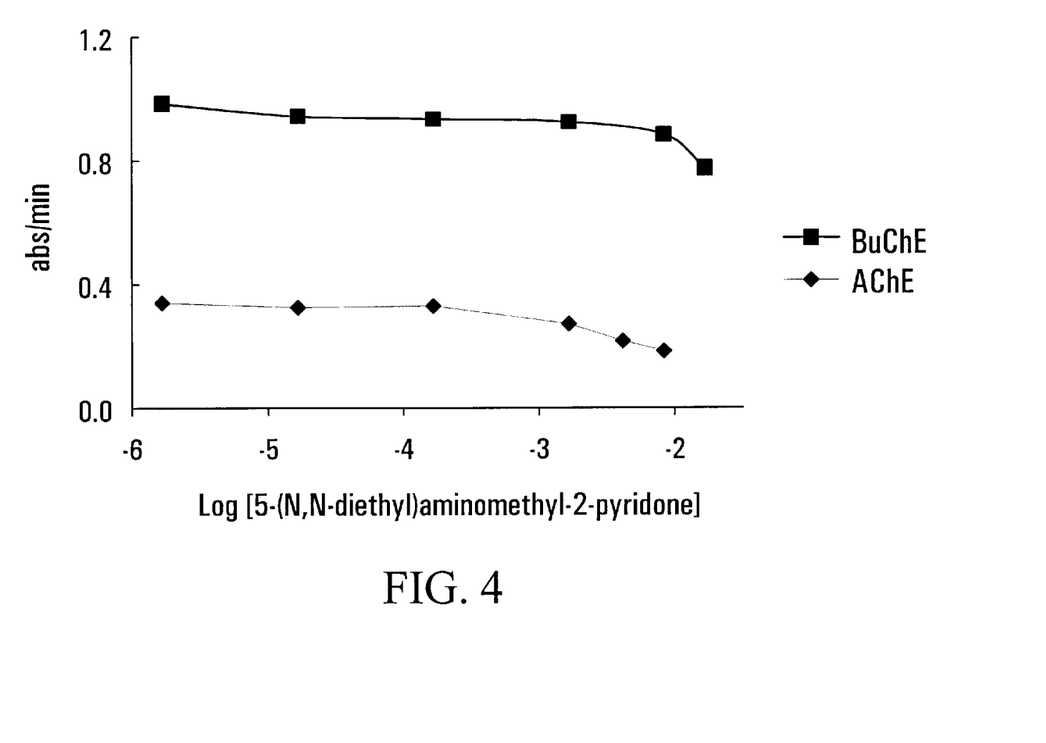
FIG. 4 is a plot of absorbance per minute against the log of concentration of 5-(N,N-diethyl)aminomethyl-2-pyridone. The graph reflects the rate of hydrolysis of the substrate (acetylthiocholine for AChE and butyrylthiocholine for BuChE).
Figure 5:
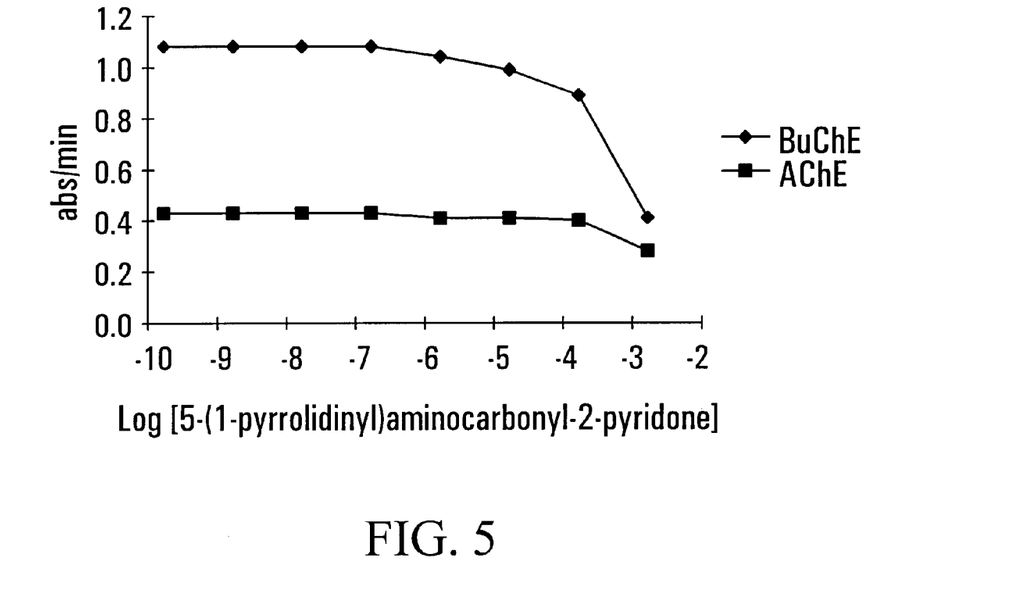
FIG. 5 is a plot of absorbance per minute against the log of concentration of 5-(1-pyrrolidinyl)carbonyl-2-pyridone. The graph reflects the rate of hydrolysis of the substrate (acetylthiocholine for AChE and butyrylthiocholine for BuChE).
Figure 6:
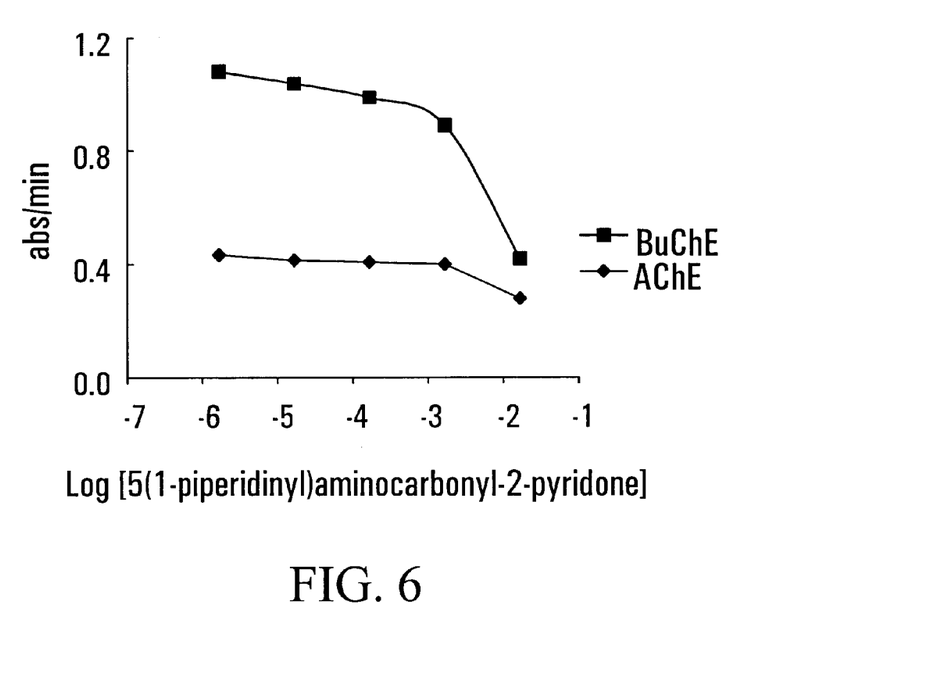
FIG. 6 is a plot of absorbance per minute against the log of concentration of 5-(1-piperidinyl)carbonyl-2-pyridone. The graph reflects the rate of hydrolysis of the substrate (acetylthiocholine for AChE and butyrylthiocholine for BuChE).
Figure 7:
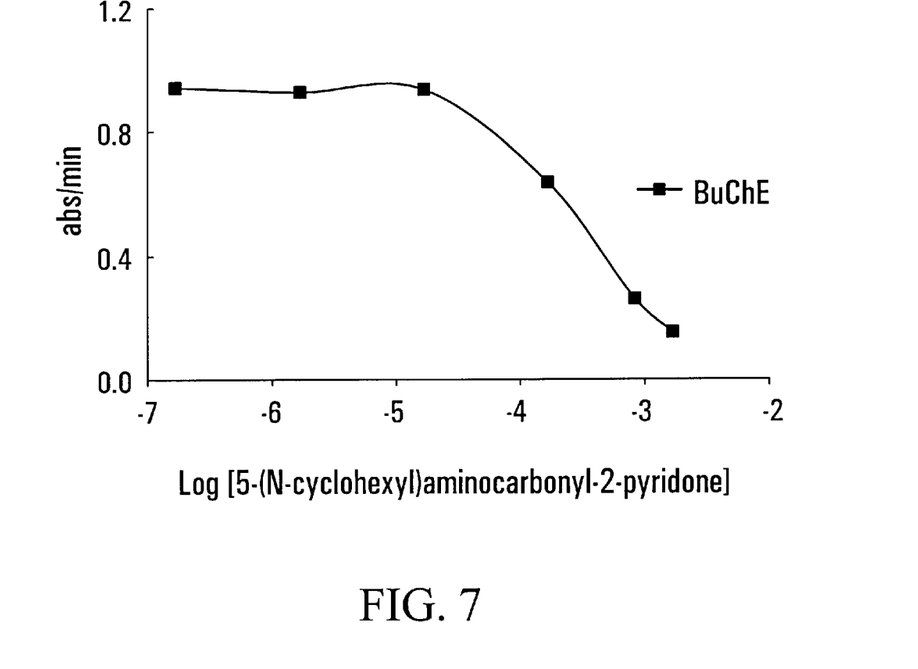
FIG. 7 is a plot of absorbance per minute against the log of concentration of 5-(N-cyclohexyl)aminocarbonyl-2-pyridone. The graph reflects the rate of hydrolysis of the substrate butyrylthiocholine by BuChE. There was no inhibition of the activity of AChE on its substrate acetylthiocholine (data not shown).
Figure 8:
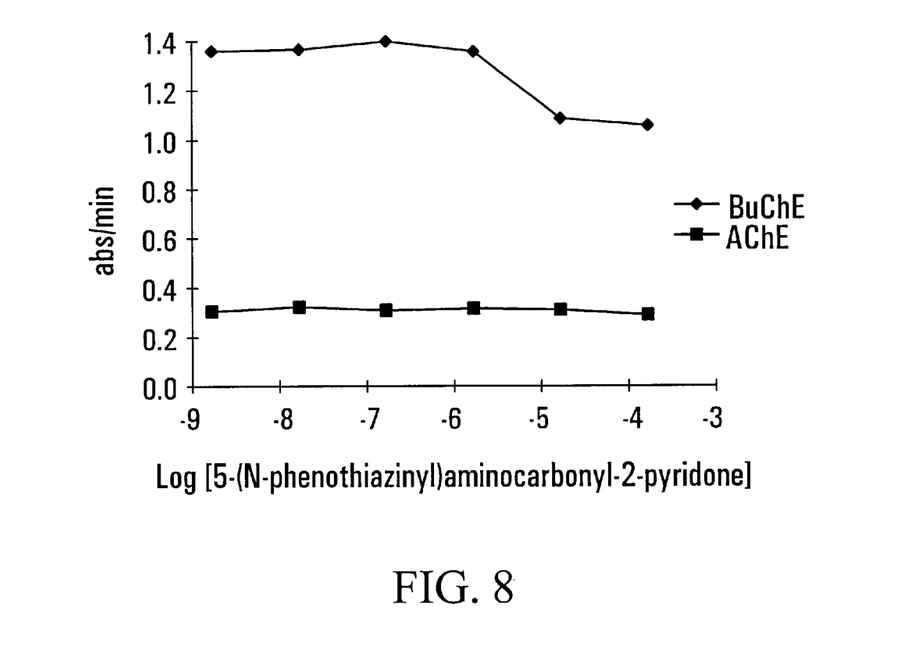
FIG. 8 is a plot of absorbance per minute against the log of concentration of 5-(N-phenothiazinyl)carbonyl-2-pyridone. The graph reflects the rate of hydrolysis of the substrate (acetylthiocholine for AChE and butyrylthiocholine for BuChE).
Figure 9:
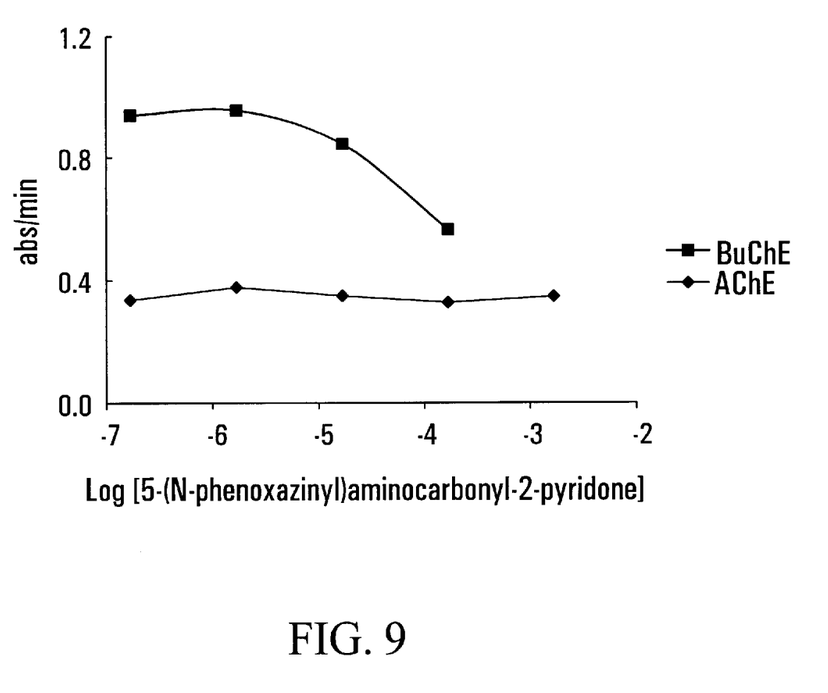
FIG. 9 is a plot of absorbance per minute against the log of concentration of 5-(N-phenoxazinyl)carbonyl-2-pyridone. The graph reflects the rate of hydrolysis of the substrate (acetylthiocholine for AChE and butyrylthiocholine for BuChE).
Figure 10:
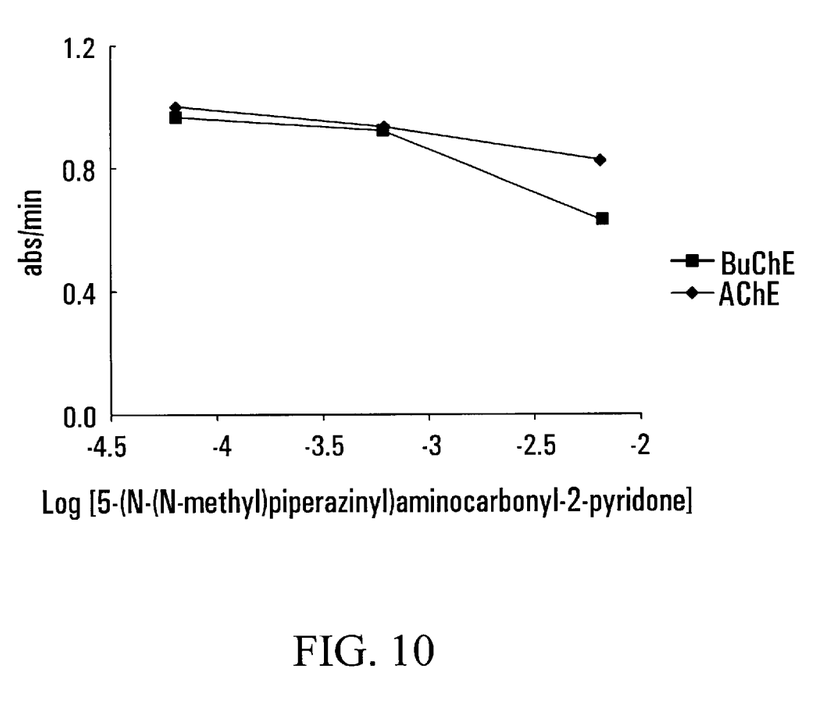
FIG. 10 is a plot of absorbance per minute against the log of concentration of 5-(N-(N-methyl)piperazinyl) aminocarbonyl-2-pyridone. The graph reflects the rate of hydrolysis of the substrate (acetylthiocholine for AChE and butyrylthiocholine for BuChE).
Figure 11:
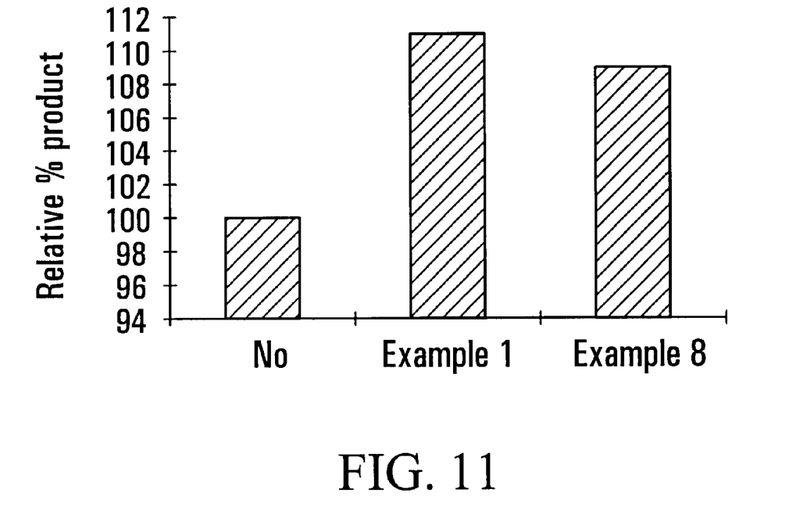
FIG. 11 is a bar diagram that shows the effect of the compounds 5-(N,N-dibenzyl)aminocarbonyl-2-pyridone (Example 1) and 5-(N-phenothiazinyl)carbonyl-2-pyridone (Example 8) on the trypsin-like activity associated with BuChE. The first bar in this figure, labeled "No", is the activity of the enzyme with trypsin-like activity associated with BuChE in the absence of any added compound.
Figure 12:
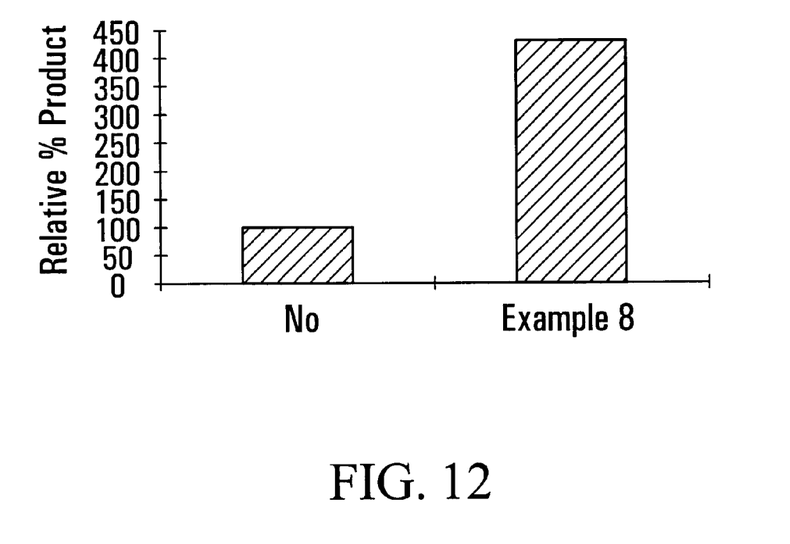
FIG. 12 is a bar diagram showing the effect of 5-(N-phenothiazinyl)carbonyl-2-pyridone (Example 8) on trypsin activity. The first bar in this figure, labeled "No", is the activity of trypsin in the absence of any added compound.

The effect of two different exemplified compounds on the enzymatic activity of the enzyme with trypsin-like activity associated with BuChE is shown in FIG. 11. The compounds of Examples 1 and 8 increased the rate of hydrolysis of trypsin substrate compound BAPNA. The effect of pyridone compounds on the enzymatic activity of trypsin itself is shown in FIG. 12. Example 8, used here as an example, substantially increased the hydrolytic activity of trypsin.

Discussion

Inhibition of Cholinesterases (Structure-activity Relationship)

The amide derivatives of 2-pyridone showed inhibitory activity towards cholinesterases. Some of the amides inhibited both AChE and BuChE to a similar extent, while others inhibited one enzyme, primarily BuChE (Table 2), more than the other. One amine derivative 5-(N,N-diethyl) aminomethyl-2-pyridone showed equal inhibitory activity towards each cholinesterase studied.

It has been shown that the active site in cholinesterases is at the bottom of a "gorge" which is lined by aromatic amino acid residues, 12 in AChE and 6 in BuChE. Some inhibitors bind to a peripheral site close to the gorge to exert their action. In the case of the 2-pyridone derivatives of the present invention, the nature of inhibition is mixed noncompetitive suggesting that these compounds most likely bind to the peripheral site near the active-site gorge. It is possible that the pyridone moiety binds at this site and the nitrogen containing side chain binds to the amino acid residues in the gorge in a reversible manner. The difference in $K_i$ values (Table 2) for the different compounds may be due to binding properties of the side chains.

Enhancement of the Activity of Serine Proteases

BuChE modifies the activity of trypsin by enhancing its activity under normal conditions (30). This suggests that alteration of a synergistic effect between BuChE and serine peptidases such as trypsin may play a significant role in maturation of plaques because it has been shown that certain biochemical properties of BuChE are altered in AD. Certain compounds of the present invention such as the phenothiazine-containing pyridone compound (Example 8) have also been found to enhance the activity of trypsin. This enhancement is most likely through interaction of this molecule with trypsin at a peripheral site, which would change the conformation of trypsin to facilitate hydrolysis of the substrate.

Other compounds of the present invention such as the dibenzyl compound (Example 1) do not have direct effect on trypsin alone. However, the activity of the above-mentioned enzyme that has trypsin-like activity and which consistently co-purifies with BuChE, is considerably enhanced by the dibenzyl compound (Example 1). This suggests that some compounds can increase the activity of the trypsin-like protein by binding with BuChE such that the compound-BuChE complex, upon binding with the trypsin-like protein, further facilitates the hydrolysis of the substrate.

Certain 2-pyridone compounds of the invention can inhibit cholinesterases. Some 2-pyridone compounds of the invention can modify the activity of other serine hydrolases such as trypsin. These serine hydrolases are thought to be involved in APP processing. Because of the enhancement of the enzymatic activity of trypsin, the 2-pyridones compounds of the present invention can be used to modify the progression of AD by modifying APP processing, a step that is thought to be the central mechanism in the pathogenesis of AD.

Cholinesterases are not only involved in cholinergic neurotransmission but also in other biological processes such as development of the nervous system (33, 34). BuChE is found in high levels during neuroblast proliferation while AChE is found in high levels during neuronal maturation (34). BuChE is found in high levels in certain tumors, particularly primary brain tumor such as gliomas. Because BuChE is involved in the process of cellular proliferation, the 2-pyridone compounds of the present invention that are specific BuChE inhibitors can be used to slow or stop growth of such brain tumors.

Glaucoma is one of the common eye diseases leading to blindness. In glaucoma, there is increased intraocular pressure. Intraocular pressure can be decreased by pupillary constriction. The pupil is innervated by both sympathetic (adrenergic)and parasympathetic (cholinergic) nervous systems. The parasympathetic nervous system, and cholinergic enhancing drugs, cause pupillary constriction which can reduce intraocular pressure. The 2-pyridone compounds of the present invention that inhibit cholinesterases and raise acetylcholine levels can be used for the treatment of ophthalmic diseases such as glaucoma.

The present invention extends to a pharmaceutical composition that comprises an active compound disclosed herein, or a pharmaceutically acceptable salt thereof, together with one or more pharmaceutically acceptable diluent or carriers, for modulating serine hydrolase activity in a mammal, preferably a human. The pharmaceutical composition can be used to treat, inhibit or prevent a pathological condition that is manifested in an abnormal concentration of, and/or activity of, a serine hydrolase enzyme. Among those pathological conditions are Alzheimer's disease, tumours such as brain tumours, for example gliomas, and glaucoma.

Thus, the active compounds of the invention may be formulated for oral, buccal, transdermal (e.g., patch), intranasal, parenteral (e.g., intravenous, intramuscular or subcutaneous), ophthalmic or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); filters (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets of lozenges formulated in conventional manner.

The active compounds of the invention may be formulated for parenteral administration by injection, including using conventional catheterization techniques or infusion. The active compounds of the invention may also be formulated for topical ophthalmic administration.

Formulations for injection or topical ophthalmic administration may be presented in unit dosage form, for example in ampules, or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient. The compounds of the invention can also be delivered in the form of an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

As used herein, the term "effective amount" means an amount of a compound of the invention that is capable of inhibiting the symptoms of a pathological condition described herein by modulation of serine hydrolase activity. The specific dose of a compound administered according to this invention will be determined by the particular circumstances surrounding the case including, for example, the compound administered, the route of administration, the state of being of the patient, and the severity of the pathological condition. A proposed dose of an active compound of the invention for oral, parenteral, buccal or topical ophthalmic administration to the average adult human for the treatment of the conditions referred to above is 0.01 to 50 mg/kg of the active ingredient per unit dose which could be administered, for example, 1 to 4 times per day.

Aerosol formulations for treatment of the conditions referred to above in the average adult human are preferably arranged so that each metered dose or "puff" of aerosol contains 20 µg to 100 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

All references cited herein are hereby incorporated by reference.

5. References

1. Mayeux R., and Sano M. (1999) Treatment of Alzheimer's disease. *New England Journal of Medicine.* 341: 1670–1679.
2. Patterson, C. J. S, Gauthier, S., Berman, H., Cohen, C. A., Feighter, J. W., Feldman, H. and Hogan, D. B. 1999. The recognition, assessment and management of dementing disorders: conclusions from the Canadian Consensus Conference on Dementia. *Canadian Medical Association Journal* 160: S1-S15.
3. Cummings, J. L., Vinters, H. V., Cole, G. M. and Khachaturian, Z. S. 1998. Alzheimer's disease: Etiologies, pathophysiology, cognitive reserve, and treatment opportunities. *Neurology* 51: S2-S17.
4. Mirra, S. S., Heyman, A., McKeel, D., Sumi, S. M., Crain, B. J., Brownlee, L. M., Vogel, F. S., Hughes, J. P., Van Belle, G., Berg, L., and participating CERAD neuropathologists. 1991. The Consortium to Establish a Registry for Alzheimer's Disease (CERAD). Part II. Standardization of the neuropathologic assessment of Alzheimer's disease. Meurology 41: 479–486.
5. Bartus, R. T., Dean, R. L., Beer, B., and Lippa, A. S. 1982. The cholinergic hypothesis of geriatric memory dysfunction. *Science* 217: 408–417.
6. Coyle, J. T., Price, D. L. and DeLong, M. R. 1983. Alzheimer's disease: A disorder of cortical cholinergic innervation. *Science* 219: 1184–1190.
7. Geula, C., and Mesulam, M—M. (1i99) Cholinesterases and the pathology of Alzheimer disease. *Alzheimer Disease and Associated Disorders* 2: 23–28.
8. Mesulam, M—M., and Geula, C. (1994) Butyrylcholinesterase reactivity differentiates the amyloid plaques of aging from those of dementia. *Annals of Neurology.* 36: 722–727.
9. Geula, C., and Mesulam, M—M. (1989) Special properties of cholinesterases in the cerebral cortex of Alzheimer's disease. *Brain Research.* 498: 185–189.
10. Greig, N. H., Lahiri, D. K., Soncrant, T. T., Utsuki, T., Yu, O. S., Shaw, K. T. Y., Holloway, H. W., Myer, R. C., Wallace, W. C., Haroutunian, V. and Ingram, D. K. 1998. Novel, selective butyrylcholinesterase (BChE) inhibitors for the treatment of Alzheimer's disease (AD). *Society for Neuroscience Abstracts* 24: 728.
11. Hardy, J. 1997 Amyloid, the presenilins and Alzheimer's disease. *Trends in Neuroscience* 20: 154–159.
12. Selkoe, D. J. 1991. The molecular pathology of Alzheimer's disease. *Neuron* 6: 487–498.
13. Guillozet, A. L., Smiley, J. F., Mash, D. C. and Mesulam, M—M. 1997. Butyrylcholinesterase in the life cycle of amyloid plaques. *Annals of Neurology* 42: 909–918.
14. Kitaguchi, N., Takahashi, Y., Tokushima, Y., Shiojiri, S. and Ito, H. 1988. Novel precursor of Alzheimer's disease amyloid protein shows protease inhibitory activity. *Nature* 331: 530–532.
15. Tanzi, R. E., McClatchey, A. I., Lamperti, E. D., Villa-Komaroff, L., Gusella, J. F. and Neve, R. L. 1988. Protease inhibitor domain encoded by an amyloid protein precursor mRNA associated with Alzheimer's disease. Nature 331:528–530.
16. Haas, C. and Selkoe, D. J. 1993. Cellular processing of β-amyloid precursor protein and the genesis of amyloid β-peptide. *Cell* 75: 1039–1042.

17. Hardy, J. 1997 Amyloid, the presenilins and Alzheimer's disease. *Trends in Neuroscience* 20: 154–159.
18. Esch, F. S., Keim, P. S., Beattie, E. C., Blacher, R. W., Culwell, A. R., Oltersdorf, T., McClure, D. and Ward, P. J. 1990. Cleavage of amyloid peptide during constitutive processing of its precursor. *Science* 248: 1122–1124.
19. Tomita, S., Kirino, Y. and Suzuki, T. 1998. A basic amino acid in the cytoplasmic domain of Alzheimer's beta-amyloid precursor protein (APP) is essential for cleavage of APP at the alpha-site. *Journal of Biological Chemistry* 273: 19304–19310.
20. Anderson, J. P., Esch, F. S., Keim, P. S., Sambamurti, K., Lieberburg, I. and Robakis, N. K. 1991. Exact cleavage site of Alzheimer amyloid precursor in neuronal PC-12 cells. *Neuroscience Letters* 128: 126–128.
21. Seubert, P., Vigo-Pelfrey, C., Esch, F., Lee, M., Dovey, H., Davis, D., Sinha, S., Schlossmacher, M., Whaley, J., Swindlhurst, C., McCormak, R., Wolfert, R., Selkoe, D. J., Lieberburg, I. and Schenk, D. 1992. Isolation and quantitation of soluble Alzheimer's β-peptide from biological fluids. *Nature* 359: 325–327.
22. Hooper, N. M., Karran, E. H. and Turner, A. J. 1997. Membrane protein secretases. *Biochemical Journal* 321: 265–279.
23. Worthington, V. 1993. Enzymes and related biochemicals. *Worthington Enzyme Manual.* Worthington Biochemical Corporation. Freehold, N.J.
24. Minn, A., Schubert, M., Neiss, W. F. and Muller-Hill, B. 1998. Enhanced GFAP expression in astrocytes of transgenic mice expressing the human brain-specific trypsinogen IV. *Glia.* 22: 338–347.
25. De Serres, M., Sherman, D., Chestnut, W., Merrill, B. M., Viveros, O. H. and Diliberto, E. J. Jr. (1993) Proteolysis at the secretase and amyloidogenic cleavage sites of the beta-amyloid precursor protein by acetyl cholinesterase and butyrylcholinesterase using model peptide substrates. *Cell Molecular and Neurobiology* 13: 279–287.
26. Meckelein, B., Marshall, D. C. L., Conn, K-J., Pietopaolo, M., Van Nostrand, W. and Abraham, C. (1998) Identification of a novel serine protease-like molecule in human brain. *Brain Research Molecular Brain Research* 55: 181–197.
27. Wiegand, U., Corbach, S., Minn, A., Kang, J. and Muller-Hill, B. 1993. Cloning of the cDNA encoding human brain trypsinogen and characterization of its product. *Gene* 136: 167–175.
28. Boopathy, R. and Balasubramanian, A. S. 1987. A peptidase activity exhibited by human serum pseudocholinesterase. *European. Journal of Biochemistry* 162: 191–197.
29. Lockridge, O. 1982. Substance P hydrolysis by human serum cholinesterase. *Journal of Neurochemistry* 39: 106–110.
30. Darvesh, S., Kumar, R., Robert, S., Walsh, R. and Martin, E. (2000) Butyrylcholinesterase-Mediated Enhancement of the Enzymatic Activity of Trypsin (In preparation).
31. Darvesh, S., Kumar, R. and Martin, E. (1999) Enzyme kinetics of butyrylcholinesterase and trypsin: Implications in Alzheimer's disease. *Canadian Journal Neurological Sciences,* 26, 546–547.
32. Ellman, G. L., Courtney, K. D., Andres, V. Jr. and Featherstone, R. M. (1961) A new and rapid calorimetric determination of acetyl cholinesterase activity. *Biochemical Pharmacology,* 7, 88–95.
33. Small, D. H., Michaelson, S. and Sberna, G. (1996) Non-classical actions of cholinesterases: Role in cellular differentiation, tumorigenesis and Alzheimer's disease. *Neurochemistry International,* 28, 453–483.
34. Layer, P. G. (1995) Non-classical roles of cholinesterases in the embryonic brain and possible links to Alzheimer disease *Alzheimer Disease and Associated Disorders,* 9, 29–36.

We claim:
1. A compound of formula I:

or a pharmaceutically acceptable salt thereof;
wherein X is C=O;
$R^3$, $R^4$ and $R^6$ are each independently selected from the group consisting of hydrogen, $(C_1-C_{12})$alkyl, substituted $(C_1-C_{12})$alkyl, $(C_3-C_8)$cycloalkyl, substituted $(C_3-C_8)$cycloalkyl, $(C_2-C_{12})$alkenyl, substituted $(C_2-C_{12})$alkenyl, $(C_2-C_{12})$alkynyl, substituted $(C_2-C_{12})$alkynyl, $(C_6-C_{14})$aryl, substituted $(C_6-C_{14})$aryl, $(C_1-C_{12})$alkyl$(C_6-C_{14})$aryl, substituted $(C_1-C_{12})$alkyl$(C_6-C_{14})$aryl, $(C_6-C_{14})$aryl$(C_1-C_{12})$alkyl, substituted $(C_6-C_{14})$aryl$(C_1-C_{12})$alkyl, $(C_6-C_{14})$aryl$(C_2-C_{12})$alkenyl, substituted $(C_6-C_{14})$aryl$(C_2-C_{12})$alkenyl, $(C_6-C_{14})$aryl$(C_2-C_{12})$alkynyl, substituted $(C_6-C_{14})$aryl$(C_2-C_{12})$alkynyl, trifluoromethyl, halogen, cyano and nitro;
—S(O)R', —S(O)$_2$R', —S(O)$_2$OR' and —S(O)$_2$NHR', wherein each R' is independently $(C_1-C_{12})$alkyl, $(C_2-C_{12})$alkenyl, $(C_2-C_{12})$alkynyl or $(C_6-C_{14})$aryl;
—C(O)R", wherein R" is selected from the group consisting of hydrogen, $(C_1-C_{12})$alkyl, substituted $(C_1-C_{12})$alkyl, $(C_3-C_8)$cycloalkyl, substituted $(C_3-C_8)$cycloalkyl, $(C_1-C_{12})$alkoxy, $(C_1-C_{12})$alkylamino, $(C_2-C_{12})$alkenyl, substituted $(C_2-C_{12})$alkenyl, $(C_2-C_{12})$alkynyl, substituted $(C_2-C_{12})$alkynyl, $(C_{6-14})$aryl, substituted $(C_6-C_{14})$aryl, $(C_6-C_{14})$aryloxy, $(C_6-C_{14})$arylamino, $(C_1-C_{12})$alkyl$(C_6-C_{14})$aryl, substituted $(C_1-C_{12})$alkyl$(C_6-C_{14})$aryl, $(C_6-C_{14})$aryl$(C_1-C_{12})$alkyl, substituted $(C_6-C_{14})$aryl$(C_1-C_{12})$alkyl, $(C_6-C_{14})$aryl$(C_2-C_{12})$alkenyl, substituted $(C_6-C_{14})$aryl$(C_2-C_{12})$alkenyl, $(C_6-C_{14})$aryl$(C_2-C_{12})$alkynyl, substituted $(C_6-C_{14})$aryl$(C_2-C_{12})$alkynyl, and trifluoromethyl;
—OR''' and —NR'''$_2$, wherein each R''' is independently selected from hydrogen, $(C_1-C_{12})$alkyl, substituted $(C_1-C_{12})$alkyl, $(C_3-C_8)$cycloalkyl, substituted $(C_3-C_8)$cycloalkyl, $(C_2-C_{12})$alkenyl, substituted $(C_2-C_{12})$alkenyl, $(C_2-C_{12})$alkynyl, substituted $(C_2-C_{12})$alkynyl, $(C_6-C_{14})$aryl, substituted $(C_6-C_{14})$aryl, $(C_1-C_{12})$alkyl$(C_6-C_{14})$aryl, substituted $(C_1-C_{12})$alkyl$(C_6-C_{14})$aryl, $(C_6-C_{14})$aryl$(C_1-C_{12})$alkyl, substituted $(C_6-C_{14})$aryl$(C_1-C_{12})$alkyl, $(C_6-C_{14})$aryl$(C_2-C_{12})$alkenyl, substituted $(C_6-C_{14})$aryl$(C_2-C_{12})$alkenyl, $(C_6-C_{14})$aryl$(C_2-C_{12})$alkynyl, substituted $(C_6-C_{14})$aryl$(C_2-C_{12})$alkynyl, $(C_6-C_{14})$aroyl, sustituted $(C_6-C_{14})$aroyl, $(C_1-C_{12})$acyl and trifluoromethyl; and
—SR'''', wherein R'''' is selected from the group consisting of hydrogen, $(C_1-C_{12})$alkyl, substituted $(C_1-C_{12})$alkyl, $(C_2-C_{12})$alkenyl, substituted $(C_2-C_{12})$alkenyl, ($C_2$–$C_{12}$)alkynyl, substituted ($C_2$–$C_{12}$)alkynyl, ($C_6$–$C_{14}$)aryl, substituted ($C_6$–$C_{14}$)aryl, ($C_1$–$C_{12}$)alkyl ($C_6$–$C_{14}$)aryl, substituted ($C_1$–$C_{12}$)alkyl($C_6$–$C_{14}$)aryl, ($C_6$–$C_{14}$)aryl($C_1$–$C_{12}$)alkyl, substituted ($C_6$–$C_{14}$)aryl ($C_1$–$C_{12}$)alkyl, ($C_6$–$C_{14}$)aryl($C_2$–$C_{12}$)alkenyl, substituted ($C_6$–$C_{14}$)aryl($C_2$–$C_{12}$)alkenyl, ($C_6$–$C_{14}$)aryl ($C_2$–$C_{12}$)alkynyl, substituted ($C_6$–$C_{14}$)aryl($C_2$–$C_{12}$) alkynyl, and trifluoromethyl; and $R^7$ and $R^8$ are each independently selected from the group consisting of hydrogen, ($C_1$–$C_{12}$)alkyl, substituted ($C_1$–$C_{12}$)alkyl, ($C_3$–$C_8$)cycloalkyl, substituted ($C_3$–$C_8$) cycloalkyl, ($C_2$–$C_{12}$)alkenyl, substituted ($C_2$–$C_{12}$) alkenyl, ($C_2$–$C_{12}$)alkynyl, substituted ($C_2$–$C_{12}$)alkynyl, ($C_6$–$C_{14}$)aryl, substituted ($C_6$–$C_{14}$)aryl, ($C_1$–$C_{12}$)alkyl ($C_6$–$C_{14}$)aryl, substituted ($C_1$–$C_{12}$)alkyl($C_6$–$C_{14}$)aryl, ($C_6$–$C_{14}$)aryl($C_1$–$C_{12}$)alkyl, substituted ($C_6$–$C_{14}$)aryl ($C_1C_{12}$)alkyl, ($C_6$–$C_{14}$)aryl($C_2$–$C_{12}$)alkenyl, substituted ($C_6$–$C_{14}$)aryl($C_2$–$C_{12}$)alkenyl, ($C_6$–$C_{14}$)aryl ($C_2$–$C_{12}$)alkynyl, substituted ($C_6$–$C_{14}$)aryl($C_2$–$C_{12}$) alkynyl, ($C_2$–$C_{14}$)heterocyclic, substituted ($C_2$–$C_{14}$) heterocyclic and trifluoromethyl;

wherein the substituted groups listed above are substituted with one or more substituents selected from the group consisting of hydroxy, ($C_1$–$C_4$)alkoxy, ($C_6$–$C_{14}$)aryl, halogen, trifluoromethyl, cyano, nitro, amino, carboxyl, carbamate, sulfonyl and sulfonamide; and the heterocyclic group contains at least one atom selected from oxygen, nitrogen and sulfur, with the proviso that when $R^7$ is hydrogen, $R^8$ is not methyl, ethyl, substituted phenyl, cyclohexyl, or a sulfur-containing five-membered heterocyclic group.

2. The compound according to claim 1, wherein $R^3$, $R^4$ and $R^6$ are each hydrogen.

3. The compound according to claim 1, wherein $R^7$ and $R^8$ are each independently selected from the group consisting of hydrogen, ($_1$–$C_{12}$)alkyl, ($C_3$–$C_8$)cycloalkyl and ($C_1$–$C_{12}$) alkyl($C_6$–$C_{14}$)aryl, with the proviso that when $R^7$ is hydrogen, $R^8$ is not methyl, ethyl, or cyclohexyl.

4. The compound according to claim 1, wherein the compound bis 5-(N,N-dibenzyl)aminocarbonyl-2-pyridone.

5. The compound according to claim 1, wherein the compound is 5-(N,N-diisopropyl)aminocarbonyl-2-pyridone.

6. The compound according to claim 1, wherein the compound is 5-(N,N-diethyl)aminocarbonyl-2-pyridone.

7. The compound according to claim 2, wherein $R^7$ and $R^8$ are each independently selected from the group consisting of hydrogen, ($C_1$–$C_{12}$)alkyl, ($C_3$–$C_8$)cycloalkyl and ($C_1$–$C_{12}$) alkyl($C_6$–$C_{14}$)aryl, with the proviso that when $R^7$ is hydrogen, $R^8$ is not methyl, ethyl, or cyclohexyl. $C_{12}$)alkyl, ($C_3$–$C_8$)cycloalkyl and ($C_1$–$C_{12}$)alkyl($C_6$–$C_{14}$)aryl, with the proviso that when $R^7$ is hydrogen, $R^8$ is not methyl, ethyl, or cyclohexyl.

* * * * *

UNITED STATES PATENT AND TRADEMARK OFFICE
CERTIFICATE OF CORRECTION

PATENT NO.    : 6,436,972 B1                                              Page 1 of 1
DATED         : August 20, 2002
INVENTOR(S)   : Sultan Darvesh et al.

It is certified that error appears in the above-identified patent and that said Letters Patent is hereby corrected as shown below:

Column 22,
Line 9, change "$(_1\text{-}C_{12})$alkyl" to -- $(C_1\text{-}C_{12})$alkyl --
Line 13, change "bis" to -- is --
Line 23, cancel beginning with "$C_{12}$)alkyl," to and including "or cyclohexyl." in column 22, line 26.

Signed and Sealed this

Twenty-second Day of July, 2003

JAMES E. ROGAN
*Director of the United States Patent and Trademark Office*